US010517722B2

(12) United States Patent
Passman et al.

(10) Patent No.: US 10,517,722 B2
(45) Date of Patent: Dec. 31, 2019

(54) DELIVERY SYSTEM FOR PROSTHETIC HEART VALVE

(71) Applicant: Edwards Lifesciences Corporation, Irvine, CA (US)

(72) Inventors: Joseph Arthur Passman, Irvine, CA (US); Linda Thai, Mission Viejo, CA (US); Michael Murad, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/469,294

(22) Filed: Mar. 24, 2017

(65) Prior Publication Data

US 2017/0273787 A1 Sep. 28, 2017

Related U.S. Application Data

(60) Provisional application No. 62/312,757, filed on Mar. 24, 2016.

(51) Int. Cl.
*A61F 2/24* (2006.01)

(52) U.S. Cl.
CPC ................... *A61F 2/2433* (2013.01)

(58) Field of Classification Search
CPC .................. A61F 2/2433; A61F 2/2436; A61F 2002/9517; A61F 2/2427; A61F 2/966; A61F 2/95

(Continued)

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 2246526 A1 | 3/1973 |
| DE | 0144167 C | 6/1985 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Eric J Rosen
*Assistant Examiner* — Andrew P. Restaino
(74) *Attorney, Agent, or Firm* — Klarquist Sparkman, LLC; Joel B. German

(57) ABSTRACT

A delivery apparatus for implanting a prosthetic implant in a native lumen of the body includes a handle portion, and a first shaft extending from and movable relative to the handle portion. The first shaft has a proximal end portion coupled to the handle portion and a distal end portion. The delivery apparatus further includes a second shaft extending from the handle portion and coaxially disposed within the first shaft. The second shaft has a proximal end portion coupled to the handle portion and a distal end portion configured to mount a prosthetic implant in a radially compressed state. The handle portion of the delivery apparatus also includes a steering assembly configured to move the first shaft longitudinally relative to the second shaft while concurrently flexing the second shaft.

12 Claims, 15 Drawing Sheets

(58) Field of Classification Search
USPC .................................................... 623/2.11
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | |
|---|---|---|
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0167955 A1* | 7/2007 | Arnault De La Menardiere ........ A61F 2/954 606/108 |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0297011 A1 | 11/2013 | Morris et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |

(56) References Cited

FOREIGN PATENT DOCUMENTS

| | | |
|---|---|---|
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A2 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006076890 A1 | 7/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2014153152 A1 | 9/2014 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 1 pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Internation Search Report for International Patent Application No. PCT/US2017024135, completed Feb. 15, 2019.

* cited by examiner

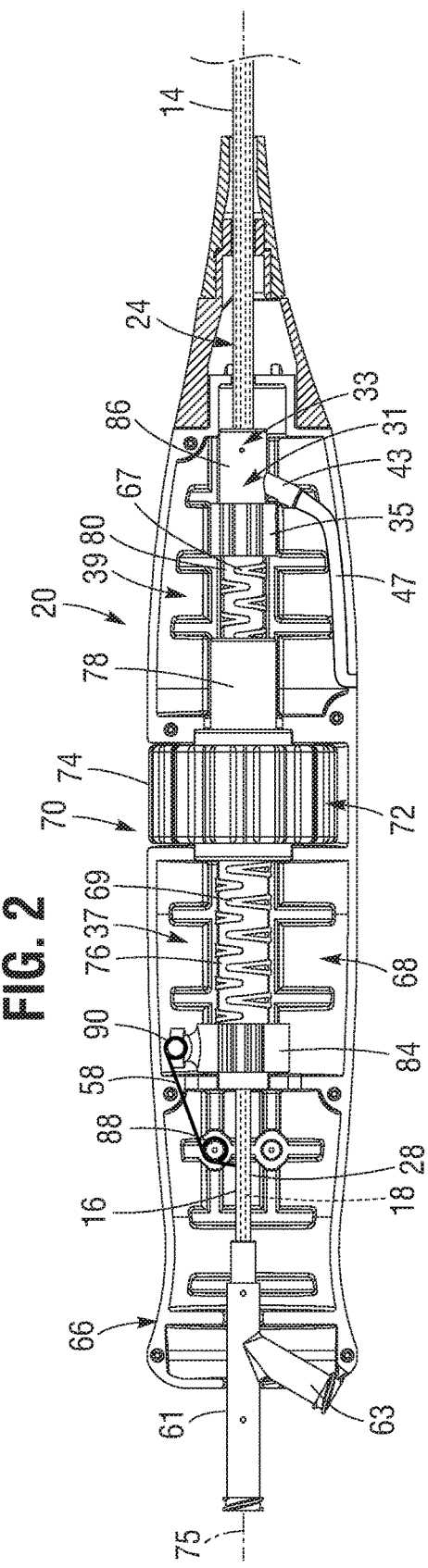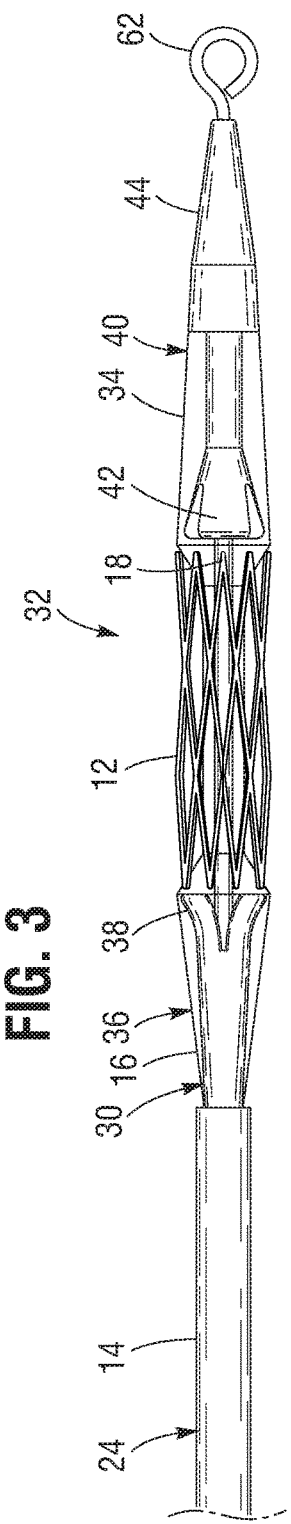
FIG. 2
FIG. 3

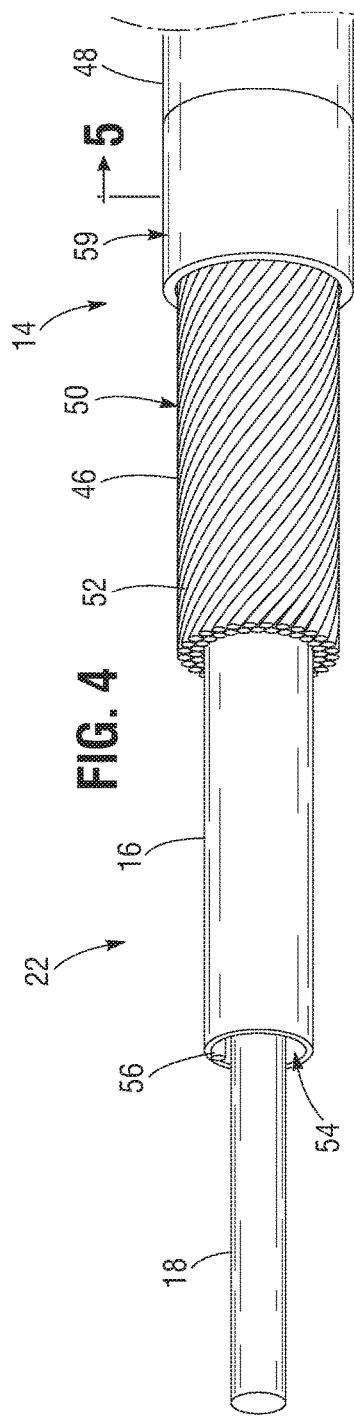
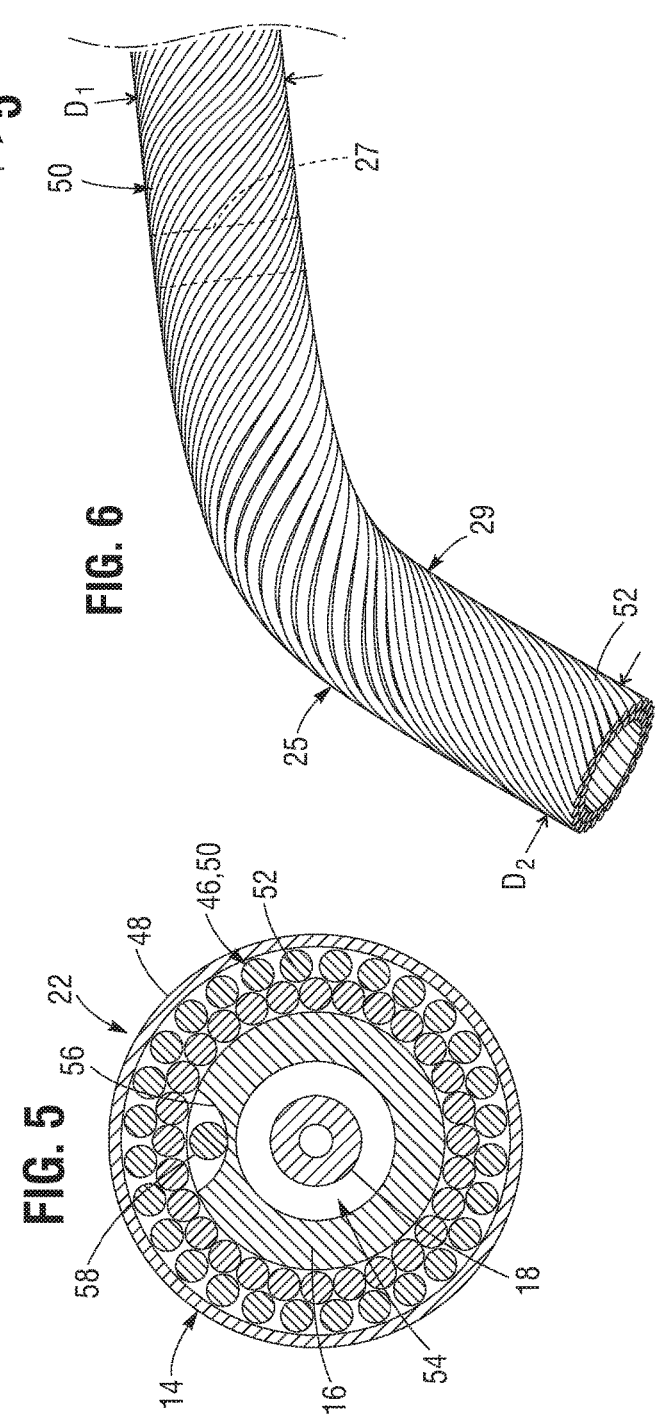
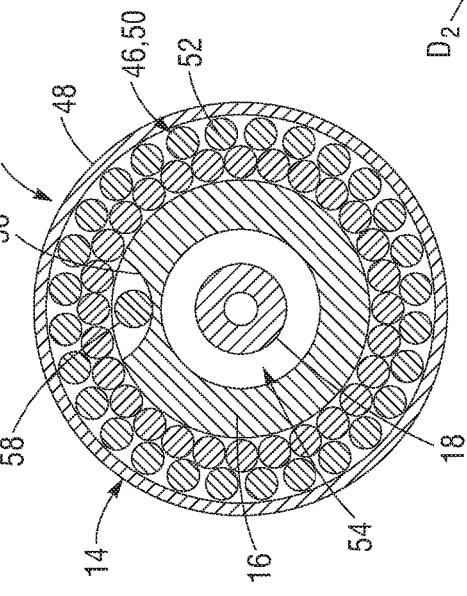

DELIVERY SYSTEM FOR PROSTHETIC HEART VALVE

CROSS REFERENCE TO RELATED APPLICATION

This application claims the benefit of U.S. Provisional Application No. 62/312,757, filed on Mar. 24, 2016, which is incorporated herein by reference.

FIELD

The present disclosure concerns embodiments of delivery systems for implanting prosthetic heart valves.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

A catheter assembly and/or a prosthetic valve that has a relatively large profile or diameter in the compressed state can inhibit the physician's ability to advance the prosthetic valve through the femoral artery or vein. More particularly, a smaller profile allows for treatment of a wider population of patients, with enhanced safety. Thus, a need exists for delivery devices that can minimize the overall crimp profile of the catheter assembly and the prosthetic valve for the delivery of the prosthetic valve through the patient's vasculature.

Relatively long delivery devices, such as used for transfemoral delivery of a prosthetic valve, can inhibit the physician's ability to position the prosthetic valve precisely at the desired implantation site because the forces applied to the handle at one end of the delivery device can cause unwanted movement of the prosthetic valve at the opposite end of the delivery device. Thus, a need exists for delivery devices that allow a physician to accurately control the positioning of the prosthetic valve at the desired implantation location.

Moreover, reducing the diameter of a catheter assembly can reduce the flexural strength of the catheter assembly, which can complicate advancement of the assembly through the body and positioning of the implant. Thus, a need exists for delivery devices with improved catheter assemblies and control mechanisms for positioning valves.

SUMMARY

Certain embodiments of the disclosure concern delivery devices for prosthetic implants. In a representative embodiment, a delivery apparatus for implanting a prosthetic implant in a native lumen of the body comprises a handle portion, and a first shaft extending from and movable relative to the handle portion. The first shaft comprises a proximal end portion coupled to the handle portion and a distal end portion. The delivery apparatus further comprises a second shaft extending from the handle portion and coaxially disposed within the first shaft. The second shaft comprises a proximal end portion coupled to the handle portion and a distal end portion configured to mount a prosthetic implant in a radially compressed state. The handle portion of the delivery apparatus further comprises a steering assembly configured to move the first shaft longitudinally relative to the second shaft while concurrently flexing the second shaft.

In another representative embodiment, a method of implanting a radially compressible and expandable prosthetic heart valve in a native valve of the heart comprises introducing a delivery device into the body of a patient, the delivery device comprising a handle portion, a first elongated shaft extending from the handle portion, and a second shaft coaxially disposed within the first shaft and having a distal end portion mounting a prosthetic heart valve in a radially compressed state. The method further comprises advancing the distal end portion of the second shaft toward the native heart valve, wherein the act of advancing comprises pushing the handle portion distally so as to push the delivery device distally through the patient toward the native heart valve. The method further comprises steering the delivery device through the patient's vasculature by operating a steering assembly coupled to the handle portion, operation of the steering assembly causing proximal or distal motion of the first shaft relative to the second shaft and concurrent flexing or unflexing of the second shaft. After the prosthetic heart valve has been moved to a desired implantation position, the method further comprises radially expanding the prosthetic heart valve to engage the annulus of the native heart valve.

The foregoing and other objects, features, and advantages of the disclosed technology will become more apparent from the following detailed description, which proceeds with reference to the accompanying figures.

BRIEF DESCRIPTION OF THE DRAWINGS

FIG. 2 is a side view of the handle portion of the delivery apparatus of FIG. 1 with a portion of the shell removed to illustrate the interior of the handle portion.

FIG. 3 is a side view of a distal end portion of the delivery apparatus of FIG. 1.

FIG. 4 is a perspective view of a representative embodiment of a catheter assembly with the components longitudinally spaced apart for purposes of illustration.

FIG. 5 is a cross-sectional view of the catheter assembly of FIG. 4 taken along line 5-5 of FIG. 4.

FIG. 6 is a perspective view of an embodiment of a tube including a flexible portion.

DETAILED DESCRIPTION

In particular embodiments, a delivery apparatus for implanting a prosthetic, transcatheter heart valve via a patient's vasculature includes a steering device for steering or adjusting the position of a balloon member including a prosthetic valve radially crimped thereon. The balloon member can be mounted on a distal end of a balloon catheter extending coaxially within another catheter. As described below in more detail, the balloon member and the crimped prosthetic valve can enter the vasculature of a patient through an introducer sheath and, once the balloon member and the crimped prosthetic valve reach a suitable location in the body, the prosthetic valve can be expanded at the treatment site (e.g., the native aortic valve). The steering device can further be used to accurately adjust or "fine tune" the position of the prosthetic valve relative to the desired deployment location.

Figure 1:
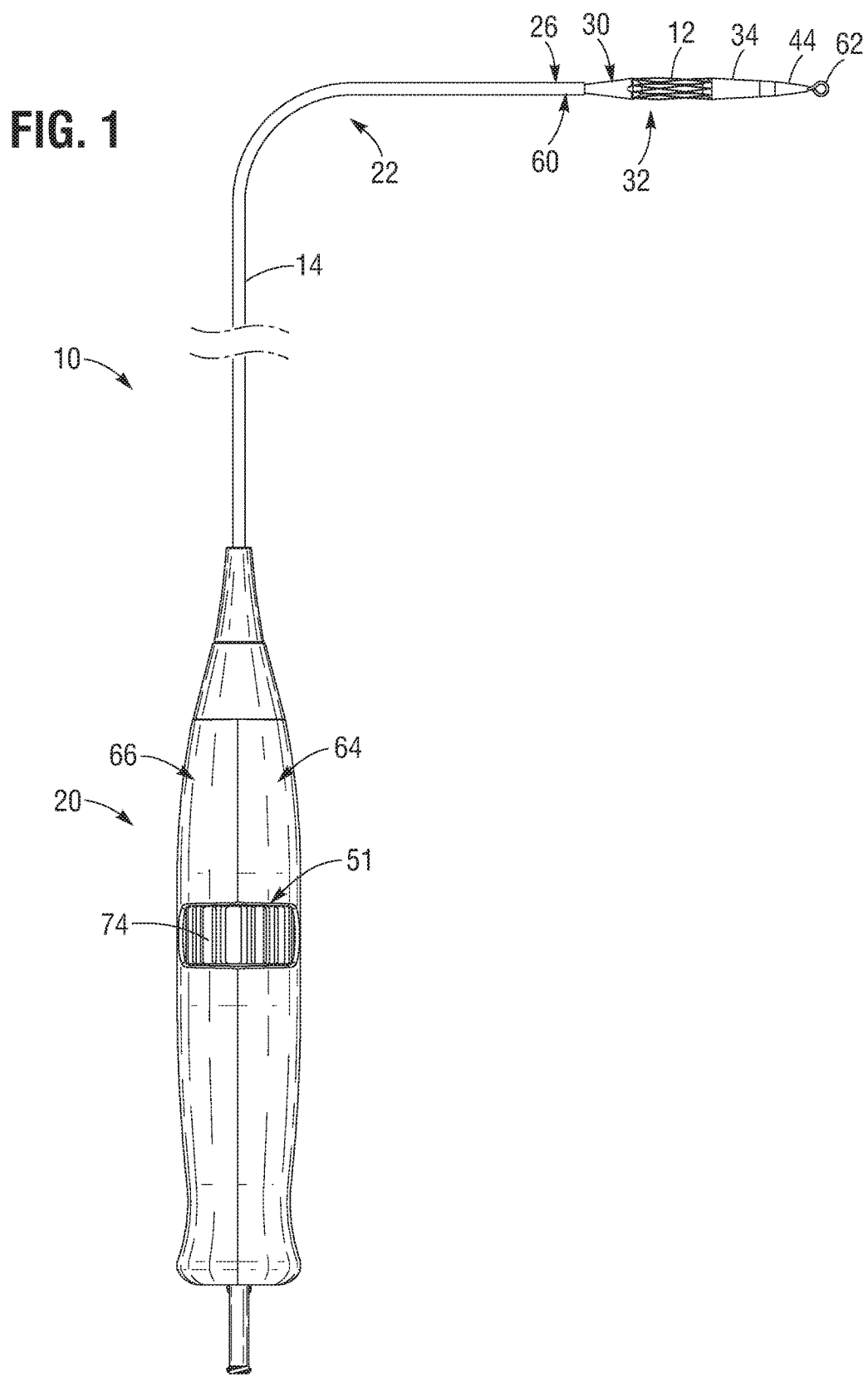
FIG. 1 is a side view of a representative embodiment of a delivery apparatus for a prosthetic implant.

FIG. 1 shows a delivery apparatus 10 adapted to deliver a prosthetic heart valve 12 (e.g., a prosthetic aortic valve) to a heart, according to one embodiment. The apparatus 10 generally includes a catheter assembly 22 having a first, outer catheter shaft 14, a second, balloon catheter shaft 16 (see, e.g., FIGS. 2 and 7) extending through the outer shaft 14, and a third, guidewire shaft 18 (FIG. 3) extending through the balloon catheter shaft 16. The outer shaft 14 and the balloon catheter shaft 16 in the illustrated embodiment are adapted to slide longitudinally relative to each other to facilitate delivery and positioning of the prosthetic valve 12 at an implantation site in a patient's body, as described in detail below.

The delivery apparatus can also include a handle portion 20 from which the catheter assembly extends. FIG. 2 shows the outer catheter shaft 14 extending from the handle portion 20 over the balloon catheter 16 and the guidewire shaft 18. In the illustrated embodiment, the outer catheter 14 can include a proximal end portion 24 disposed inside the handle portion 20, and a distal end portion 26 (see, e.g. FIG. 1). The balloon catheter shaft 16 can also include a proximal end portion 28 disposed inside the handle portion 20, and a distal end portion 30 configured to mount the prosthetic valve 12 in a radially compressed state.

Referring to FIG. 3, the distal end portion 30 of the balloon catheter shaft 16 can comprise a balloon mounting portion 32 configured to support an inflatable balloon 34. A proximal end portion 36 of the balloon can be folded around a proximal shoulder member 38 (also referred to as a "stop") of the balloon mounting portion 32 mounted on the end of the balloon catheter shaft 16 and a distal end portion 40 of the balloon 34 can be folded around a distal shoulder member 42 of the balloon mounting portion mounted on the distal end portion of the guidewire shaft 18. In certain embodiments, the distal end of the outer shaft 14 terminates proximal to the proximal end of the balloon 32. In the illustrated embodiment, the proximal end portion 36 of the balloon 34 is secured to the balloon catheter shaft 16. The distal end portion 40 of the balloon can be secured to a nose cone 44 disposed on or otherwise coupled to the guidewire shaft 18.

Turning to the catheter assembly 22 in more detail, FIG. 4 illustrates the components of the catheter assembly longitudinally spaced apart for purposes of illustration. FIG. 5 is a cross-sectional view of the catheter assembly 22 taken along line 5-5 of FIG. 4. In certain embodiments, the outer shaft 14 can comprise an inner layer 46 and an outer layer 48. In some embodiments, the inner layer 46 can be configured to provide axial strength or stiffness to the outer shaft to reduce the tendency of the outer shaft to flex under axial loads (e.g., when pushing the catheter assembly through a patient's vasculature), while the outer layer 48 can be more flexible than the inner layer. For example, in the illustrated embodiment, the inner layer is configured as a tube 50 defined by a plurality of helically wound filaments or filars 52 (e.g., Helical Hollow Strand® tube available from Fort Wayne Metals Research Products Corp.). The filars 52 can be made of any of various biocompatible metals such as stainless steel, titanium, nickel-titanium alloys (e.g., Nitinol), etc.

In the illustrated embodiment, the tube 50 can include an inner and outer layer of filars 52. However, it should be understood that the tube 50 can include any suitable number of layers of filaments, such as a single layer or three layers.

The filars 52 can have a round cross-section, or any other suitably-shaped cross-section. Additionally, the filars 52 can have uniform diameters, or non-uniform diameters. For example, the diameter of the filars can vary between the inner and outer layer of filars, and/or the diameter can vary radially about the cross-section of the tube 50, or longitudinally along its length, depending upon the particular properties desired. In alternative embodiments, the tube 50 can be a braided metal wire tube, or any other construction exhibiting suitable stiffness properties. For example, in some embodiments, the tube 50 can be made from braided metal wire (e.g., 304 grade stainless steel flat wire and/or round wire braids in a one-over-one pattern). In alternative embodiments, the tube 50 can be an extruded polymer tube or a laser-cut metal tube, such as a laser-cut hypotube including one or more cut patterns along its length, or a tube made of any other suitable material with a relatively higher durometer than the balloon catheter shaft 16.

The outer layer 48 covering the tube 50 can be a polymeric covering, such as a polyether block amide (commercially available as Pebax®), nylon, or any other suitable biocompatible polymer. In some embodiments, the outer layer 48 can have a longitudinally varying hardness or durometer. For example, the durometer of the outer layer 48 can be relatively higher at the proximal end portion 24 of the outer catheter and relatively lower at the distal end portion 26 to provide, for example, flexural stiffness to the outer catheter 14 at the proximal end and greater flexibility at the distal end portion. In a representative example, the proximal end portion can be made from a material (e.g., a Nylon 12 material such as Grilamid TR55LX) having a relatively higher durometer (e.g., about 72 D), and the distal end portion can made from a material (e.g., Pebax®) having a relatively lower durometer (e.g., about 55 D). In some embodiments, the outer layer 48 can include a durometer transition region 59 located at the distal end of the outer layer where the outer layer transitions from a relatively higher durometer to a relatively lower durometer. In alternative embodiments, the outer layer 48 can be disposed inside the tube 50. In further alternative embodiments, the outer shaft 14 can include a polymeric layer on the interior and on the exterior of the tube 50, as desired.

The balloon catheter shaft 16 can be coaxially disposed within the outer shaft 14. The outer shaft 14 can be movable relative to the balloon catheter shaft 16, as described in greater detail below. Thus, either or both of the balloon catheter shaft 16 and the outer shaft 14 can include a low-friction coating, such as polytetrafluoroethylene (PTFE) or fluorinated ethylene propylene (FEP), to promote sliding of the shafts relative to one another. Referring to FIG. 5, the balloon shaft can define a lumen or fluid passageway 54 that is fluidly connectable to a fluid source (e.g., saline) to inflate the balloon and flush the space between the balloon shaft and the guidewire shaft. For example, in the illustrated embodiment, the proximal end portion 28 of the balloon catheter shaft 16 can be coupled to a branched connector member 61 (FIG. 2). The connector member 61 can include a first tubular portion 63 in fluid communication with the lumen 54 of the balloon shaft. Fluid (e.g., from an external fluid source) can flow through the tubular portion 63 of the connector member 61, through the lumen 54 of the balloon shaft, and through passages in the proximal and distal shoulders 38 and 42 of the balloon mounting portion 32 (FIG. 3). The fluid can then flow into the proximal and distal end portions 36, 40 of the balloon 34 to inflate the balloon and expand the valve 12.

Figure 12:
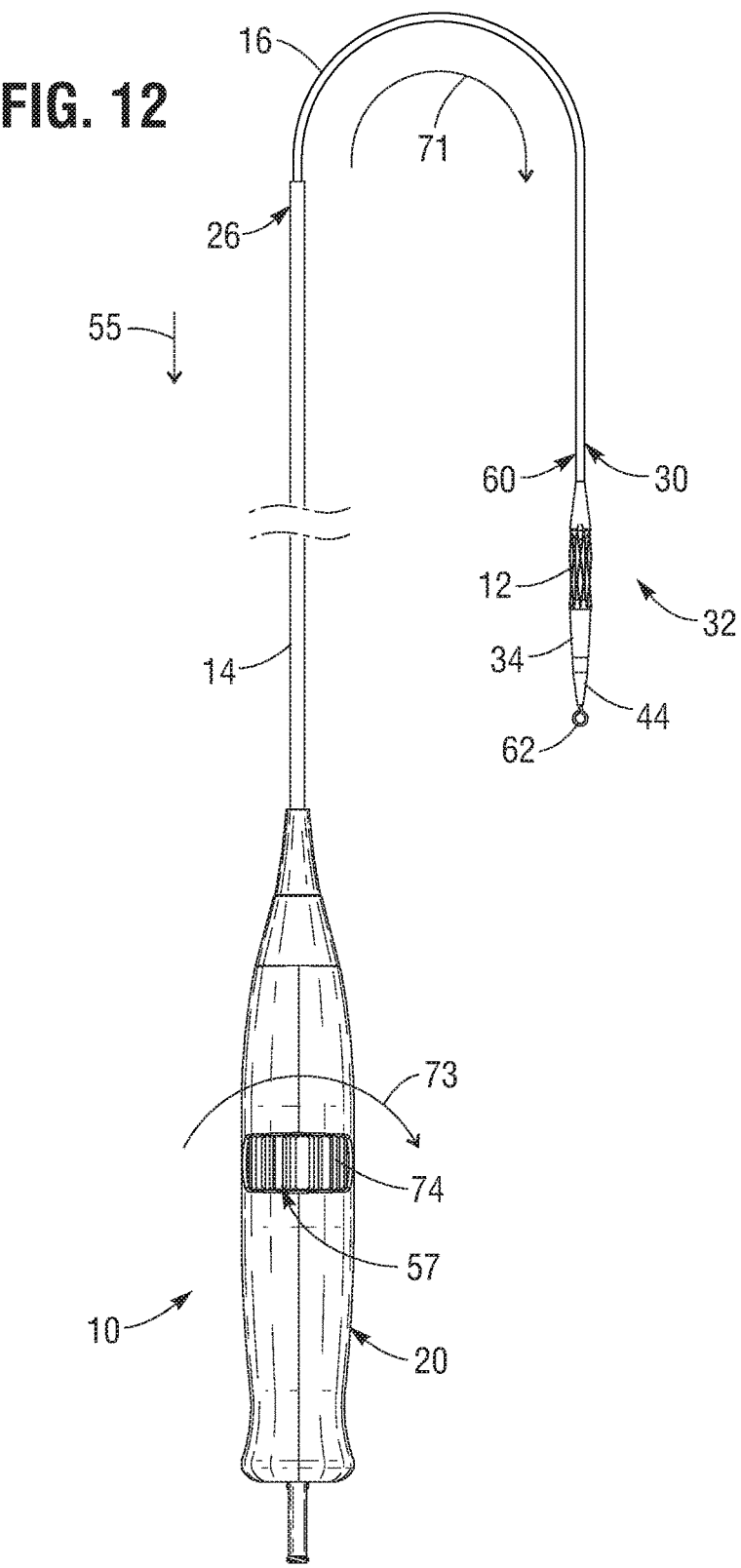
FIG. 12 is a side view of the delivery apparatus of FIG. 1 with a balloon shaft in a flexed state and an outer shaft in a retracted position.

In the illustrated embodiment, the balloon catheter shaft 16 can also define a pull wire lumen 56 through which a pull wire 58 (see, e.g., FIGS. 2 and 7) can extend between the handle portion and a pull wire attachment portion 60 at or near the distal end of the balloon catheter shaft (see, e.g., FIGS. 1 and 12). Tensioning or releasing the pull wire 58 can allow an operator to adjust the curvature of the catheter assembly to assist in guiding the apparatus through the patient's vasculature and, in particular, the aortic arch, as further described below. In some embodiments, the pull wire lumen 56 can also include an anti-friction coating (e.g., PTFE or FEP) to reduce sliding friction between the lumen and the pull wire 58.

The balloon catheter shaft 16 can be flexible such that tensioning or releasing the pull wire 58 causes flexing or unflexing of the balloon shaft. Thus, the balloon catheter shaft 16 can be made from any of various suitable materials, such as braided or coiled stainless steel wires or combinations thereof, or any of various biocompatible polymeric materials such as nylon or polyether block amides (e.g., Pebax®). In some embodiments, the balloon catheter shaft 16 can have longitudinal sections formed from different materials in order to vary the flexibility of the shaft along its length.

The guidewire shaft 18 can be coaxially disposed within the balloon catheter shaft 16, and can define a lumen for receiving a guidewire 62 (see, e.g., FIGS. 1 and 3). The guidewire shaft 18 can be configured to flex with the balloon catheter shaft 16 upon application or release of tension on the pull wire 58. In the illustrated embodiment, the connector member 61 can include a second tubular portion 65 defining a lumen in communication with the lumen of the guidewire shaft 18 through which the guidewire 62 can be inserted. The guidewire shaft 18 can be made from suitably flexible materials, such as nylon, braided stainless steel wires, or polymeric materials, similar to the balloon shaft. The interior surface of the guidewire shaft can also include an anti-friction coating (e.g., PTFE) to reduce sliding friction between the lumen and the guidewire 62, and may be formed with longitudinal sections having different degrees of flexibility corresponding to, for example, the balloon catheter shaft 16.

FIG. 6 illustrates another configuration of the tube 50 of the outer shaft 14 wherein a distal end portion 25 of the tube includes a retaining portion 27. In certain embodiments, the retaining portion 27 can be configured as, for example, a retaining member such as a metal ring secured inside the lumen of the tube (e.g., by welding). In certain embodiments, the retaining portion 27 can be a region where the filars 52 are welded together or otherwise joined to one another. The portions of the filars 52 located distally of the retaining portion 27 can then be separated or unwound (e.g., by cutting the distal end portion of the tube 50 and partially unwinding the filars) to define a relatively more flexible portion 29. The distal tip ends of the filars 52 can then be re-welded to one another such that the filars are coupled to one another at their respective distal tip ends and at the retaining portion 27, but not coupled to one another along the length of the flexible portion 29. In this manner, the portions of the filars in the flexible portion 29 can move independently relative to one another and separate from one another as the tube 50 bends or flexes as shown in FIG. 6, thereby providing a greater degree of flexibility to the distal end portion of the outer shaft 14 without substantially compromising the axial stiffness of the outer shaft.

In certain embodiments, unwinding the filars 52 in the flexible portion 29 can also result in greater spacing between adjacent filars, and/or can allow the pitch of the portions of the filars in the flexible region to vary relative to the pitch of the portions of the filars proximal of the flexible region. For example, by unwinding the filars in the flexible region, the pitch of the portions of the filars in the flexible region can vary with flexing and unflexing of the tube 50 relative to the pitch of the portions of the filars outside of the flexible portion.

The tube configuration of FIG. 6 can be used with any of the catheter shaft and/or delivery handle embodiments described herein. Additionally, the flexible portion 29 need not be confined to the distal end of the tube 50, but can extend along any suitable portion of the length of the tube, including along the entire length of the tube, as desired. In some embodiments, the distal end portion of the tube 50 can be shape-set to have a predetermined curvature, as shown in FIGS. 1 and 6. In embodiments including the flexible portion 29, the flexible portion can also be shape-set such that it has a predetermined curvature. Alternatively, the tube 50 can be straight without any preset curvature.

In further embodiments, the filars 52 can have a reduced thickness along a length of the distal end portion 25 of the tube 50 such that the tube has a reduced outer diameter to promote flexibility. For example, in some embodiments, the thickness of the filars at the distal end portion of the tube can decrease as a function of length such that the diameter of the tube 50 reduces from a first outer diameter $D_1$ to a second outer diameter $D_2$ (FIG. 6). In this manner, the distal end portion of the tube 50 can have a tapered profile, and the flexibility of the distal end portion of the tube can be improved. In an exemplary embodiment, the outer diameter of the tube 50 can decrease from about 0.155 inch to about 0.135 inch over a length of about 15 cm, about 10 cm, or about 5 cm from the distal end of the tube. This reduction in outer diameter can be achieved by, for example, grinding the filars along their length to achieve the desired thickness, or by otherwise varying the thickness of the filar strands at the distal end portion of the tube.

Figure 7:
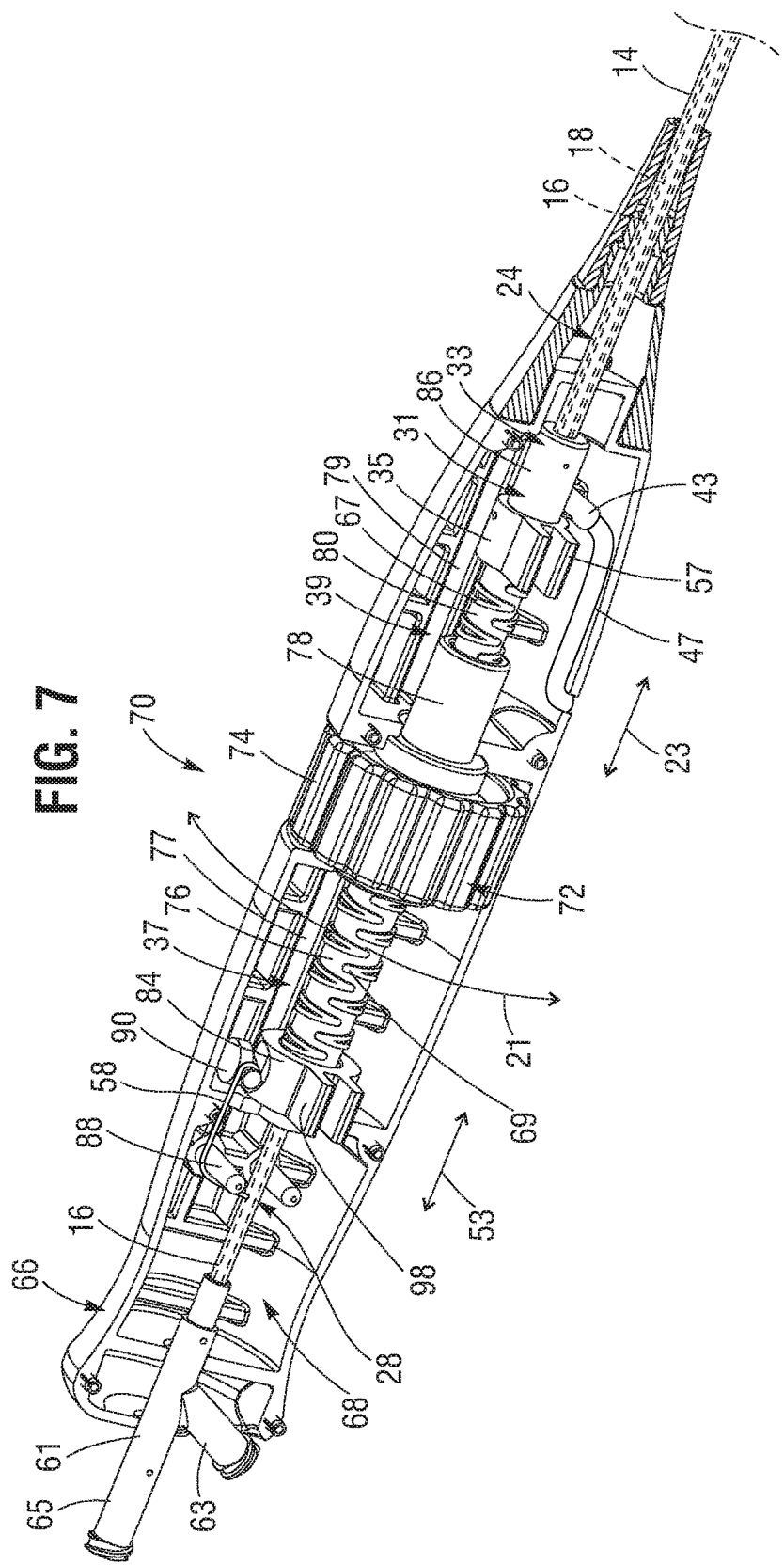
FIG. 7 is a perspective view of the handle portion of the delivery apparatus of FIG. 1 with a portion of the shell removed to illustrate the interior of the handle portion.

Referring again to FIGS. 1 and 2, the handle portion 20 in the illustrated embodiment can comprise first and second shell portions 64, 66 coupleable to one another to define an interior cavity 68 (FIGS. 2 and 7). As best shown in FIGS. 2 and 7, the handle portion 20 can include a steering assembly 70 for steering the delivery apparatus through a patient's vasculature (e.g., the aortic arch) and positioning the balloon and prosthetic valve in the annulus of a native heart valve. The steering assembly 70 can include a control member configured as a rotatable member 72 including a knob portion 74, a first threaded shaft 76, and an internally-threaded tubular portion 78 configured to receive a second threaded shaft 80. In the illustrated embodiment, the rotatable member 72 and the first threaded shaft 76 can be part of a balloon shaft-flexing sub-assembly 37, and the second threaded shaft 80 can engage with the rotatable member as part of an outer shaft-moving sub-assembly 39. In the illustrated embodiment, the balloon shaft-flexing sub-assembly 37 and the outer shaft-moving sub-assembly 39 can be jointly operable by rotation of the rotatable member, as described in greater detail below.

Figure 8:
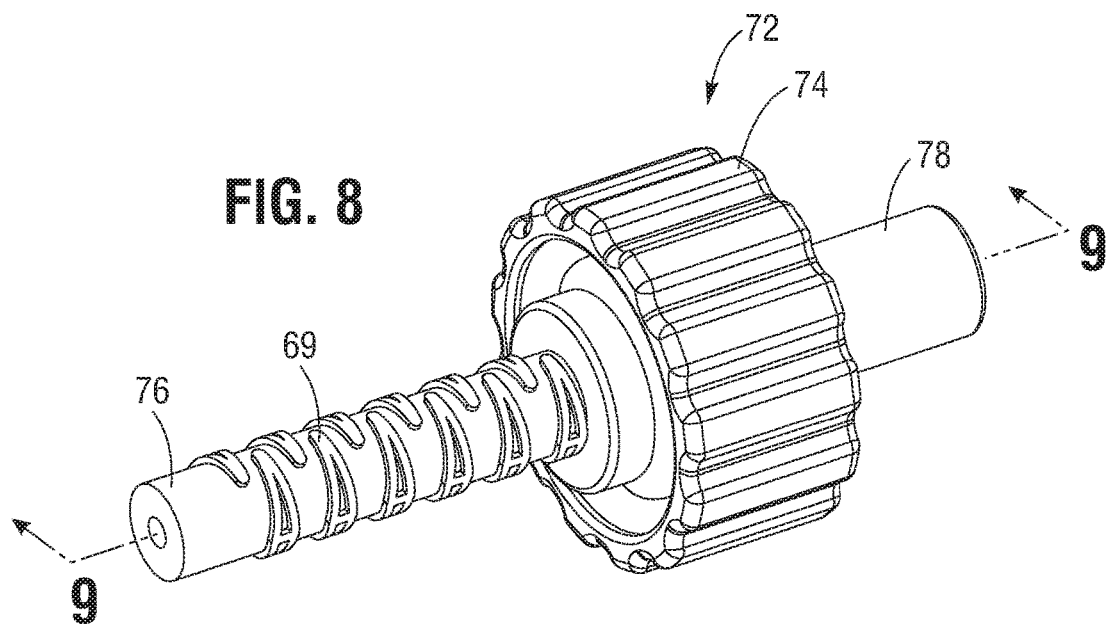
FIG. 8 is a perspective view of a representative embodiment of a rotatable member.
Figure 9:
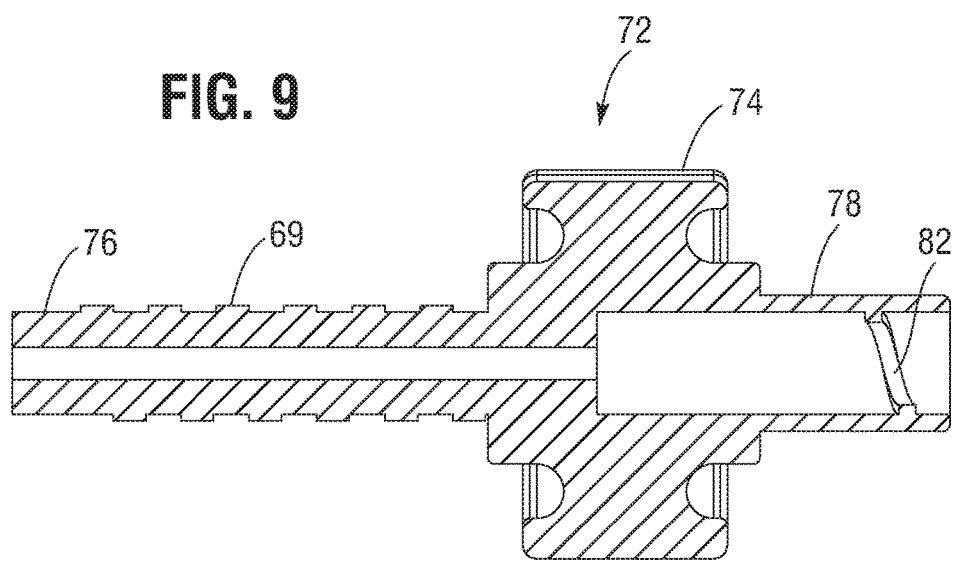
FIG. 9 is a cross-sectional side view of the rotatable member of FIG. 8 taken along line 9-9 of FIG. 8.

FIGS. 8 and 9 illustrate the rotatable member 72 in greater detail. In the illustrated embodiment, the first threaded shaft 76 and the tubular portion 78 are integrally formed with the knob portion 74. However, it should be understood that the knob portion 74, the first threaded shaft 76 and/or the tubular portion 78 can also be separately formed components. Additionally, although the rotatable member 72 is illustrated with the first threaded shaft 76 extending proximally from the knob portion 74, it should be understood that the orientation of the rotatable member can be reversed without substantially altering its principle of operation.

The rotatable member 72 and the first and second threaded shafts 76, 80 can be disposed coaxially about the balloon catheter shaft 16. As stated above, the second threaded shaft 80 can be received in the tubular portion 78 of the rotatable member as a part of the outer shaft-moving sub-assembly 39. The tubular portion 78 of the rotatable member can include internal threads 82 (FIG. 9) defined on the inner surface of the tubular portion that can engage external threads 67 on the exterior of the second threaded shaft 80. In this manner, rotation of the rotatable member 72 in the directions indicated by double-headed arrow 21 (FIG. 7) causes corresponding rotation of the first threaded shaft 76 about the balloon catheter shaft 16 in the same direction. Rotation of the rotatable member 72 also causes longitudinal motion of the second threaded shaft 80 along the balloon catheter shaft in the directions of double-headed arrow 23 between a proximal position and a distal position.

Referring again to FIG. 7, the balloon shaft-flexing sub-assembly 37 of the steering assembly 70 can further include a pull wire coupling member 84 movably disposed on the first threaded shaft 76. In the illustrated embodiment, the pull wire 58 can exit the pull wire lumen 56 of the balloon catheter shaft 16 adjacent the proximal end portion 28 of the balloon catheter shaft. Tracing the pull wire 58 from the location at which it exits the balloon catheter shaft, the pull wire 58 can extend radially away from the balloon catheter shaft and wrap at least partially around a pull wire guide member configured as a post 88. In the illustrated embodiment, the pull wire guide member 88 extends into the cavity 68 from the second shell portion 66 of the handle in a direction generally perpendicular to a longitudinal axis 75 (FIG. 2) of the handle portion. A proximal portion of the wire can be fixedly secured to a mounting portion 90 of the pull wire coupling member 84. In the illustrated embodiment, the pull wire guide member 88 can guide the pull wire 58 radially away from the balloon catheter shaft 16 to the pull wire coupling member 84. It should be understood that the pull wire guide member 88 need not be configured as a post, but can be, for example, a ramp member, or any other suitable structure.

Figure 10:
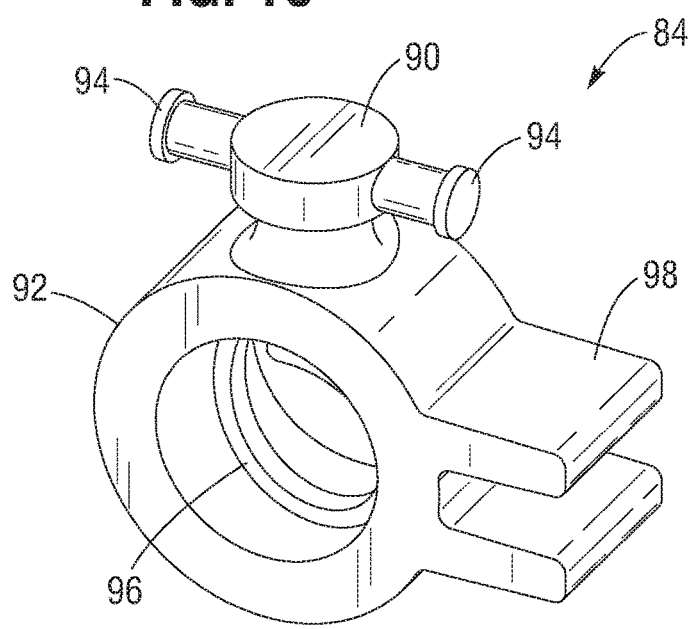
FIG. 10 is a perspective view of a representative embodiment of a pull wire coupling member.

FIG. 10 illustrates the pull wire coupling member 84 in greater detail. In the illustrated embodiment, the pull wire coupling member 84 can include a tubular main body portion 92 from which the mounting portion 90 extends. The mounting portion 90 can include one or more pull wire attachment members configured as projection members 94 (e.g., two in the illustrated configuration) to which the pull wire 58 can be tied or otherwise attached. An inner surface of the main body portion 92 can define threads 96 that can engage exterior threads 69 of the first threaded shaft 76. In this manner, rotation of the first threaded shaft 76 can cause corresponding longitudinal motion of the pull wire coupling member 84 along the first threaded shaft between a proximal position and a distal position in the directions indicated by double-headed arrow 53 (FIG. 7). This longitudinal motion of the pull wire coupling member can increase or decrease tension in the pull wire 58, thereby flexing or unflexing the balloon shaft 16. Thus, the proximal position of the pull wire coupling member 84 can correspond to a substantially slackened state of the pull wire 58 and an unflexed state of the balloon shaft 16 (absent any shape-set curvature of the catheter assembly) and the distal position of the pull wire coupling member can correspond to a tensioned state of the pull wire and a fully flexed state of the balloon shaft (see, e.g., FIG. 12).

The pull wire coupling member can also include a pair of extension portions 98 defining a groove therebetween. In the assembled state, the groove can receive a guide member configured as a tab or extension portion coupled to the first shell portion 64, similar to the extension portion 77 coupled to the second shell portion 66 illustrated in FIG. 7. The extension portion can extend parallel to the first threaded shaft 76, and can have a length corresponding substantially to a permissible length of travel of the pull wire coupling member 84 along the first threaded shaft 76. By receiving the extension portion of the handle shell, the extension portions 98 can prevent rotation of the pull wire coupling member 84 as it moves along the length of the threaded shaft 76. In alternative embodiments, the extension portions 98 can be located on the opposite side of the pull wire coupling member 84 such that they engage the extension portion 77. In further alternative embodiments, the pull wire coupling member 84 can include extension portions 98 on both sides to engage respective extension portions of the first and second shell portions of the handle.

Returning to FIG. 7, the outer shaft-moving sub-assembly 39 can include an outer shaft coupling member 86 disposed about the balloon catheter shaft 16. The outer shaft coupling member 86 can include a proximal end portion 31 and a distal end portion 33. The proximal end portion 31 can be coupled to a guide member 35, and the distal end portion 33 can be configured to receive the outer shaft 14. The guide member 35 can be disposed on the distal end of the second threaded shaft 80 such that longitudinal motion of the second threaded shaft 80 caused by rotation of the rotatable member 72 in turn causes corresponding longitudinal motion of the guide member 35 in the directions of double-headed arrow 23 (FIG. 7). This, in turn, causes longitudinal motion of the outer shaft coupling member 86 and the outer shaft 14 between the proximal position and the distal position. Thus, the proximal position of the outer shaft-moving sub-assembly 39 can correspond to a proximal position of the outer shaft 14 relative to the balloon catheter shaft 16, and the distal position of the sub-assembly 39 (the position illustrated in FIG. 7) can correspond to a distal position of the outer shaft 14 relative to the balloon catheter shaft 16. In the illustrated embodiment, the guide member 35 can include extension portions 57 similar to the extension portions 98 of the pull wire coupling member 84. The extension portions 57 can receive a guide member extending from the wall of the first shell 64 similar to the extension portion 79 of the second shell portion 66 such that the second threaded shaft 80 is prevented from rotating as it translates longitudinally relative to the rotatable member. In alternative embodiments, the extension portions 57 can also be located on the opposite side such that they engage the extension portion 79, and/or the guide member 35 can include extension portions on both sides to engage the respective extension portions of the first and second handle portions.

Figure 11:
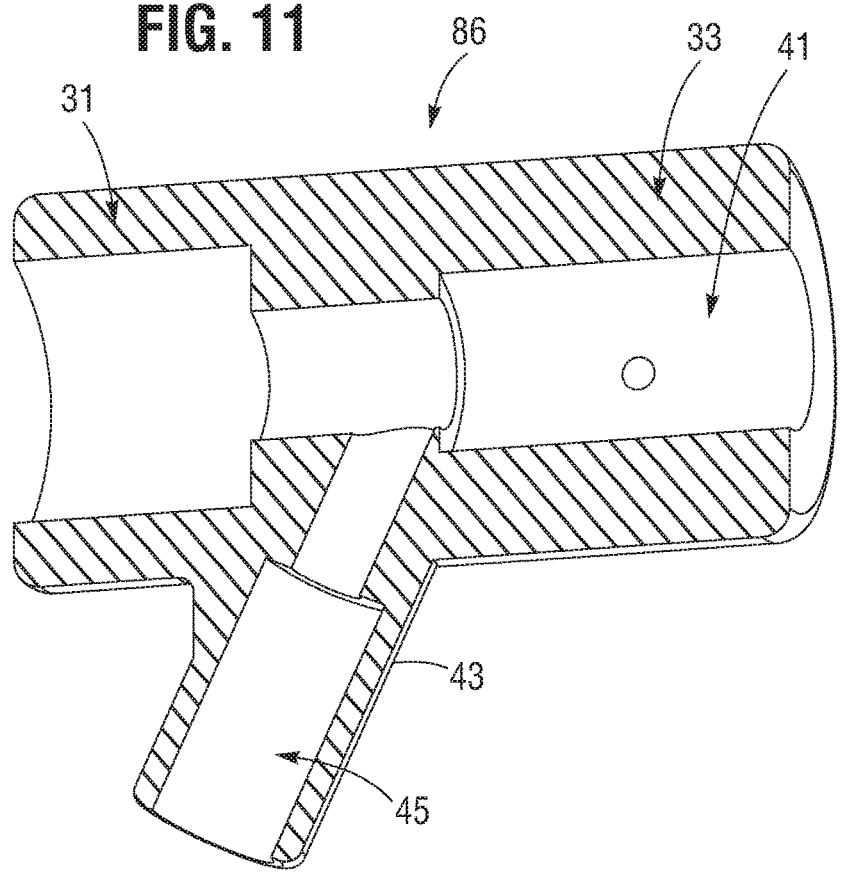
FIG. 11 is a cross-sectional perspective view of an outer shaft coupling member.

FIG. 11 illustrates a cross-sectional view of the outer shaft coupling member 86 in greater detail. The distal end portion 33 can define a lumen 41 configured to receive and retain the proximal end portion of the outer shaft 14. A flush port 43 can extend from the coupling member 86, and can define a lumen 45 in fluid communication with the outer shaft 14. The flush port 43 can connect with a tube 47 (FIG. 7) that exits the handle portion and that can, in turn, be connected to a stopcock, fluid source, etc., outside the handle. The balloon catheter shaft 16 can extend through the outer shaft coupling member 86 uninterrupted and can extend through a sealing member (not shown) disposed between the outer shaft coupling member 86 and the guide member 35 to seal the lumen of the outer shaft coupling member.

Returning to FIG. 1, the rotatable member 72 can be accessible through an opening 51 defined on a side portion of the assembled handle portion. This can allow the rotatable member to be operated by the thumb, finger(s), or a combination thereof, of one hand.

As described above, the balloon shaft-flexing sub-assembly 37 and the outer shaft-moving sub-assembly 39 of the steering assembly 70 can be jointly operable by rotation of the rotatable member 72. FIG. 1 illustrates the delivery apparatus with the outer shaft 14 in the distal position relative to the balloon catheter shaft 16. Rotation of the rotatable member 72 in a first direction (e.g., clockwise from the perspective of a user in the direction of arrow 73 of FIG. 12) can cause clockwise rotation of the first threaded shaft 76 and corresponding distal motion of the pull wire coupling member 84 along the threaded shaft 76. This, in turn, can apply tension to the pull wire 58 as the pull wire coupling member 84 moves along the threaded shaft 76, causing the balloon catheter shaft 16 to flex such that the balloon mounting portion 32 is deflected or curved in the direction indicated by arrow 71 of FIG. 12. Conversely, rotation of the knob 74 in the opposite direction can advance the outer shaft 14 relative to the balloon catheter shaft 16 and return the balloon catheter shaft to a non-deflected state.

Simultaneously, rotation of the rotatable member 72 can cause corresponding proximal motion of the second threaded shaft 80 and the outer shaft coupling member 86 with respect to the rotatable member. This, in turn, can cause proximal motion of the outer shaft 14 relative to the balloon catheter shaft 16 in the direction of arrow 55 of FIG. 12 while the balloon catheter shaft is being flexed.

The simultaneous flexing of the balloon catheter shaft 16 and retraction of the outer shaft 14 enabled by the embodiments described herein, as well as the catheter assembly configurations, can provide significant advantages. For example, by making the outer shaft 14 relatively stiffer or less flexible than the balloon catheter shaft 16, the outer shaft can provide columnar strength and resistance to buckling in axial loading situations when it is disposed over the length of the balloon catheter shaft in the distal position. This can reduce or eliminate undesirable buckling of the catheter assembly as it is advanced through narrow passages, such as through an introducer sheath or through narrow vessels in the body. The catheter configurations described herein can also allow the outer diameter of the catheter assembly 22 to be reduced (e.g., to 12 Fr or less), while providing suitable axial stiffness properties during insertion and flexibility properties when steering. In alternative embodiments, the outer shaft 14 need not be stiffer than the balloon catheter shaft 16. Nonetheless, the outer shaft enhances the overall rigidity along the distal end portion of the catheter assembly when the outer shaft is in the distal position.

Once inside the body, the ability to simultaneously retract the outer shaft 14 when the balloon catheter shaft 16 is flexed can enhance the degree of flexure achievable by the balloon catheter shaft, allowing the catheter assembly to be steered through tortuous anatomy such as the aortic arch. Concurrently retracting the outer shaft 14 while flexing the balloon catheter shaft 16 can also offer improvements in the ability to control the position of the balloon mounting portion 32. For example, due to the relatively higher stiffness of the outer shaft 14 as compared to the balloon catheter shaft 16 (or due to the relatively higher stiffness of the combination of the outer shaft and the balloon catheter shaft as compared to the balloon catheter shaft alone), the location of the distal end portion 26 of the outer shaft relative to the balloon catheter shaft can determine the point at which the balloon catheter shaft begins to bend, or its "flex point." This is illustrated in FIG. 12, in which the outer shaft 14 and the portion of the balloon catheter shaft 16 disposed within the outer shaft are relatively straight (absent any shape-set curvature), and the balloon catheter shaft begins to flex at the point at which it emerges from the distal end portion of the outer shaft. Retracting the outer shaft while flexing the balloon catheter shaft can also allow the user to more precisely control the radius of curvature of the balloon catheter shaft, as well as the degree of flexion of the balloon catheter shaft.

The embodiments described herein can also provide improved repeatability in bending location or "flex point" of the balloon catheter shaft, along with the degree of bending of the balloon catheter shaft, among different users. Stated differently, because the balloon shaft-flexing sub-assembly and the outer shaft-moving sub-assembly are mechanically linked, the balloon catheter shaft can be induced to flex at the same location and achieve substantially the same degree of curvature for a given position of the outer shaft relative to the balloon catheter shaft, even when the delivery apparatus is operated by different users.

It should be understood that the embodiments described herein are not limited to the particular configurations shown. For example, in the illustrated embodiment, the balloon shaft-flexing sub-assembly 37 is located proximally of the outer shaft-moving sub-assembly 39 inside the handle portion 20. However, it should be understood that in alternative embodiments the position of the respective sub-assemblies can be reversed. Additionally, although the first threaded shaft 76 is longitudinally fixed relative to the knob portion 74 while the second threaded shaft 80 is longitudinally movable, it should be understood that this configuration can be reversed. Furthermore, motion of the rotatable member 72 can be transmitted to the various components of the respective sub-assemblies 37, 39 by other than the threaded shafts 76, 80. For example, in some embodiments the respective sub-assemblies can include gears, levers, or other mechanisms for transmitting motion in lieu of, or in combination with, the threaded shafts. Such elements can be used to, for example, decouple the rate at which the balloon shaft is flexed from the rate at which the outer shaft is retracted. In other embodiments, the steering assembly can include multiple pull wires that attach at the same or different locations along the length of the balloon catheter shaft 16 to, for example, facilitate flexing of the balloon catheter shaft or portions thereof in multiple directions.

Figure 13:
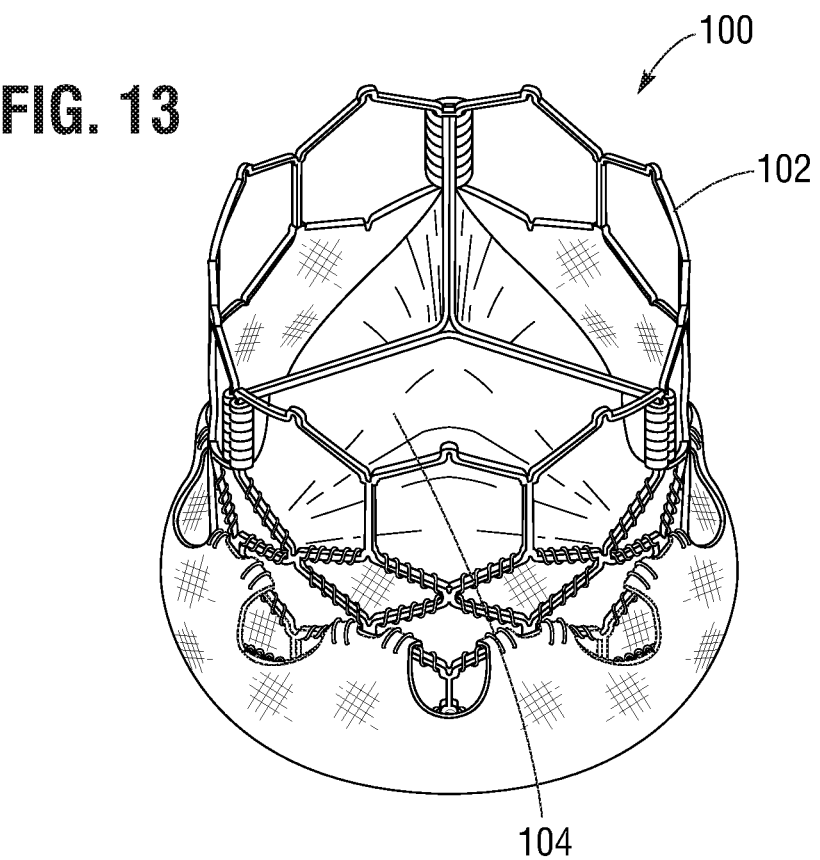
FIG. 13 is a perspective view of a representative embodiment of a prosthetic heart valve.
Figure 14:
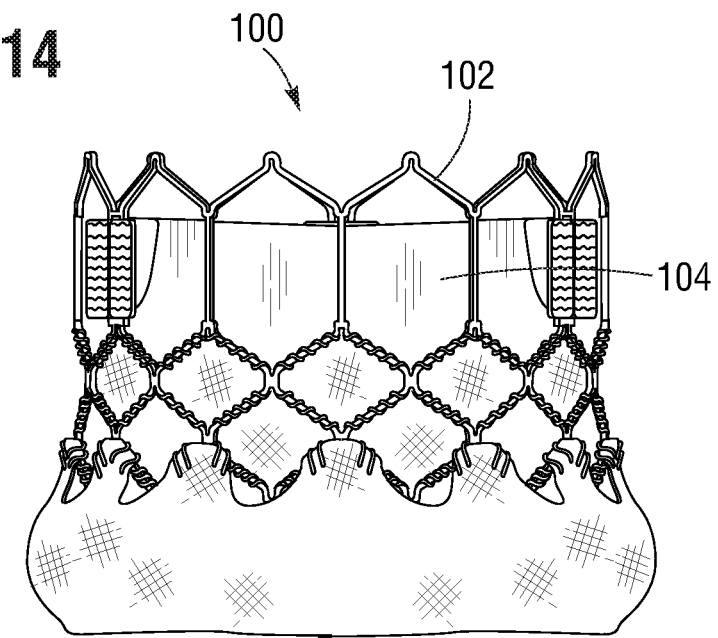
FIG. 14 is a side elevation view of the prosthetic heart valve of FIG. 13.

FIGS. 13 and 14 show a prosthetic heart valve 100, according to one embodiment, that can be used with the delivery apparatus 10. The prosthetic heart valve 100 comprises a frame, or stent, 102 and a leaflet structure 104 supported by the frame. In particular embodiments, the heart valve 100 is adapted to be implanted in the native aortic valve and can be implanted in the body using, for example, the delivery apparatus 10 described above. The prosthetic valve 100 can also be implanted within the body using any of the other delivery apparatuses described herein. Thus, the frame 102 typically comprises a plastically expandable material, such as stainless steel, a nickel based alloy (e.g., a nickel-cobalt-chromium alloy), polymers, or combinations thereof. In other embodiments, the prosthetic valve 100 can be a self-expandable prosthetic valve with a frame made from a self-expanding material, such as Nitinol. When the prosthetic valve is a self-expanding valve, the balloon of the delivery apparatus can be replaced with a sheath or similar restraining device that retains the prosthetic valve in a radially compressed state for delivery through the body. When the prosthetic valve is at the implantation location, the prosthetic valve can be released from the sheath, and therefore allowed to expand to its functional size. It should be noted that any of the delivery apparatuses disclosed herein can be adapted for use with a self-expanding valve. In one implementation, for example, the balloon catheter shaft can be replaced with a shaft having a distal end portion that comprises a sheath sized to contain the prosthetic valve in its radially compressed state. The handle of the delivery apparatus can be configured to retract the shaft relative to the prosthetic valve to deploy the valve from the sheath.

Figure 15:
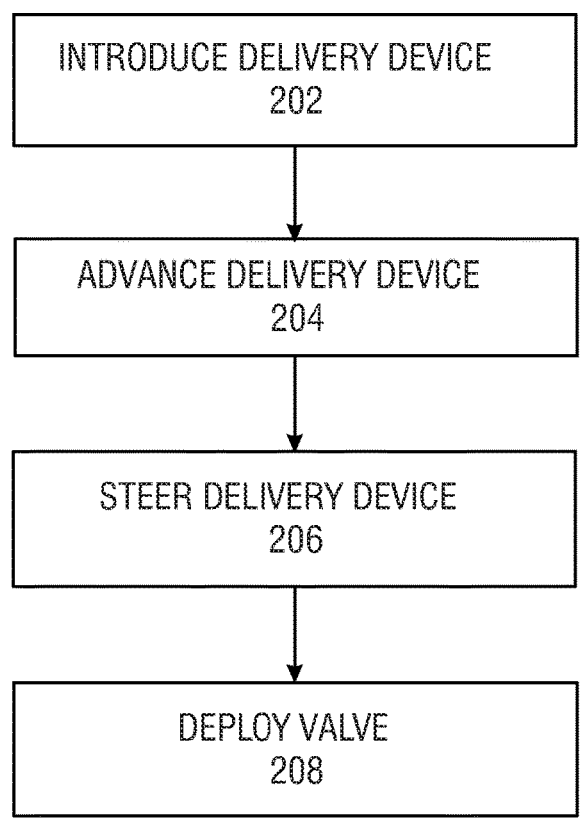
FIG. 15 is a process flow diagram illustrating a representative method of using a delivery apparatus.

FIG. 15 illustrates a representative embodiment of a method of implanting a prosthetic heart valve using the delivery devices disclosed herein. At block 202, a delivery device can be introduced into the body of a patient via, for example, an incision in the femoral artery. The delivery device can comprise a handle portion, a first elongated shaft extending from the handle portion, and a second shaft coaxially disposed within the first shaft and having a distal end portion mounting a prosthetic heart valve in a radially compressed state.

At block 204, the distal end portion of the second shaft can be advanced toward the native heart valve, wherein the act of advancing comprises pushing the handle portion distally so as to push the delivery device distally through the patient toward the native heart valve.

At block 206, the device can be steered through the patient's vasculature by operating a steering assembly coupled to the handle portion. Operation of the steering assembly can cause proximal or distal motion of the first shaft relative to the second shaft and concurrent flexing or unflexing of the second shaft.

At block 208, after the prosthetic heart valve has been moved to the desired implantation position, the prosthetic heart valve can be radially expanded to engage the annulus of the native heart valve, such as by inflating a balloon or by deploying the valve from a sheath.

Figure 16:
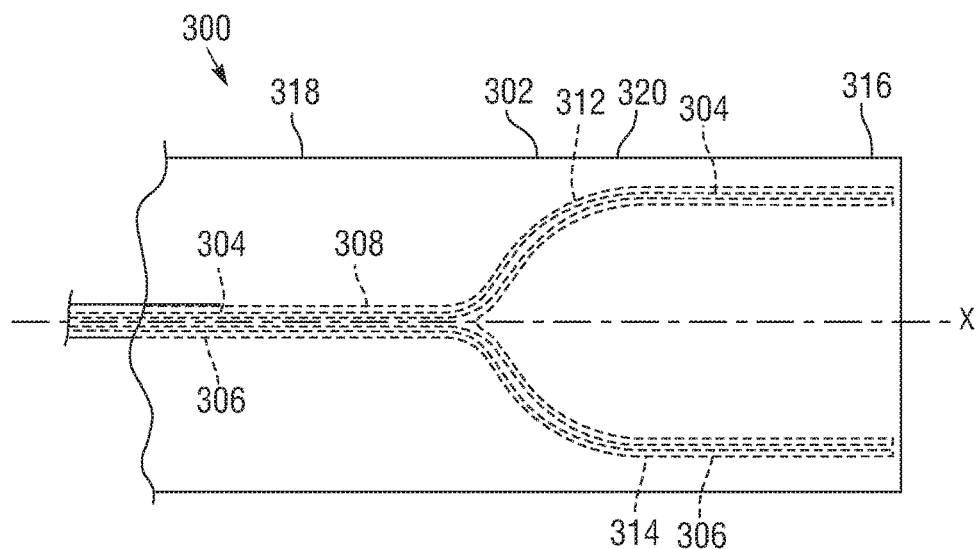
FIG. 16 is a schematic side view of a distal end portion of a catheter device, according to another embodiment, having two pull wires that extend through a central proximal lumen and two distal lumens.

FIG. 16 shows a catheter device 300, according to another embodiment. The catheter device 300 in the illustrated embodiment comprises a first pull wire 304, a second pull wire 306, and a shaft 302 having a proximal portion 315 (FIG. 20) and a steerable distal portion 316. In the illustrated embodiment, the distal portion 316 can be relatively more flexible than the proximal portion 315. The proximal portion 315 can be coupled to a handle (not shown) that can have one or more adjustment mechanisms (e.g., similar to the steering assembly 70) for increasing and decreasing tension in the pull wires 304, 306. In particular embodiments, the catheter device 300 can have two adjustment mechanisms, each of which is connected to a respective pull wire 304, 306. An example of a catheter device with two adjustment mechanisms is described in U.S. Patent Application Publication No. 2013/0030519, which is incorporated herein by reference in its entirety.

The main body 310 can further comprise a main pull-wire lumen 308 extending parallel to a central axis X of the shaft through the proximal portion 315 and through a proximal section 318 of the distal portion 316. The main pull-wire lumen 308 can then split into a first distal pull-wire lumen 312 and a second distal pull-wire lumen 314 that diverge away from each other and then extend generally parallel to each other at angularly spaced locations through a distal section 320 of the distal portion 316 of shaft. The pull wires 304, 306 can thus extend through the main pull-wire lumen 308 over the proximal portion 315 and the proximal section 318 of the distal portion 316 of the shaft. The first and second pull wires 304, 306 then part ways to extend into the first distal pull-wire lumen 312 and the second distal pull-wire lumen 314, respectively, over the distal section 320 of the distal portion 316.

Figure 17:
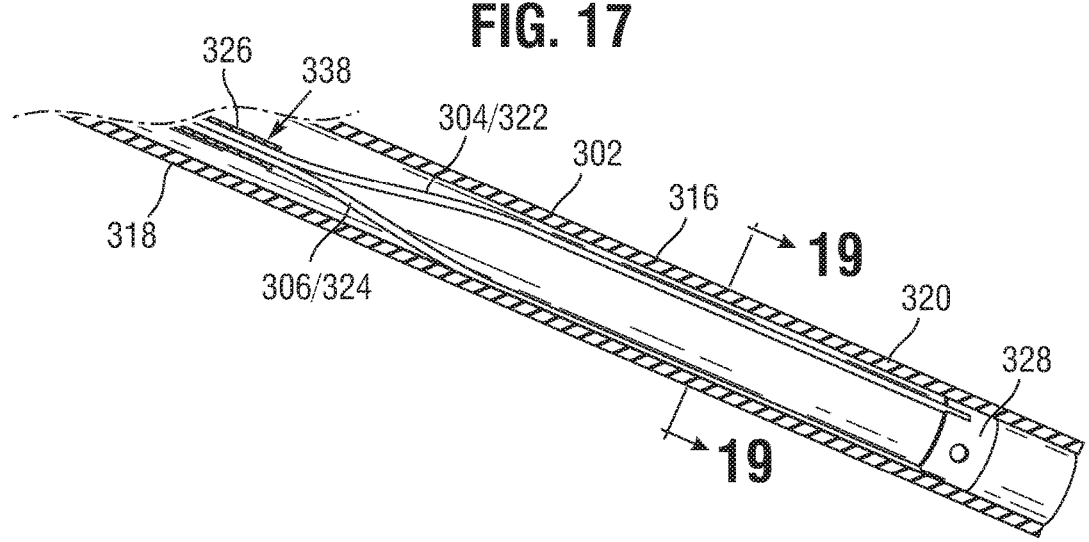
FIG. 17 is a cross-sectional side view of a distal end portion of another embodiment of the catheter device of FIG. 16.

FIG. 17 illustrates another embodiment of the catheter device 300 in which the first pull wire 304 is coaxially disposed in, and movable relative to, a first pull-wire lumen 322, and the second pull wire 306 is coaxially disposed in, and movable relative to, a second pull-wire lumen 324. The pull-wire lumens 322, 324 can be coextensive with the pull wires 304, 306 along substantially the entire length of the pull wires. Thus, portions of the following description proceed with reference only to the lumens 322, 324 for clarity, but the described locations, directional changes, etc., of the pull-wire lumens 322, 324 are applicable to the respective pull wires 304, 306 as well, and vice versa, unless stated otherwise. Additionally, in other embodiments, the pull wires 304, 306 need not include lumens.

The pull-wire lumens 322, 324 can be disposed in a pull-wire conduit 326 that is incorporated into the wall of the shaft and extends through the proximal portion 315 and the proximal section 318 of the distal portion 316 of the shaft. The pull-wire conduit 326 can then terminate at distal end portion 338, and the pull-wire lumens 322, 324 can extend from the conduit 326 and diverge away from each other about the circumference of the shaft 302. The pull-wire lumens 322, 324 can then extend generally parallel to each other at angularly spaced locations through the distal section 320. The pull wires 304, 306 can extend from their respective lumens where they can be coupled to a pull ring 328 at or near the distal end of the catheter shaft 302, and can act on the pull ring 328 when tensioned to steer the catheter shaft, as further described below. In other embodiments, the pull-wire lumens 322, 324 can be grouped together in the proximal portion 315 and the proximal section 318, and need not include a separate pull-wire conduit.

In some embodiments, the catheter shaft 302 can comprise a plurality of layers of different materials and/or materials having different durometers or bending properties. For example, with reference to FIGS. 18 and 19, the distal portion 316 of the shaft 302 can include a first or outer layer 330, a second layer 332, and a third or inner layer 334 (FIG. 19). In the illustrated embodiment, the inner and outer layers 334, 330 can be, for example, any of a variety of flexible polymeric material such as Pebax®, and/or lubricious materials such as polytetrafluoroethylene (PTFE).

Figure 18:
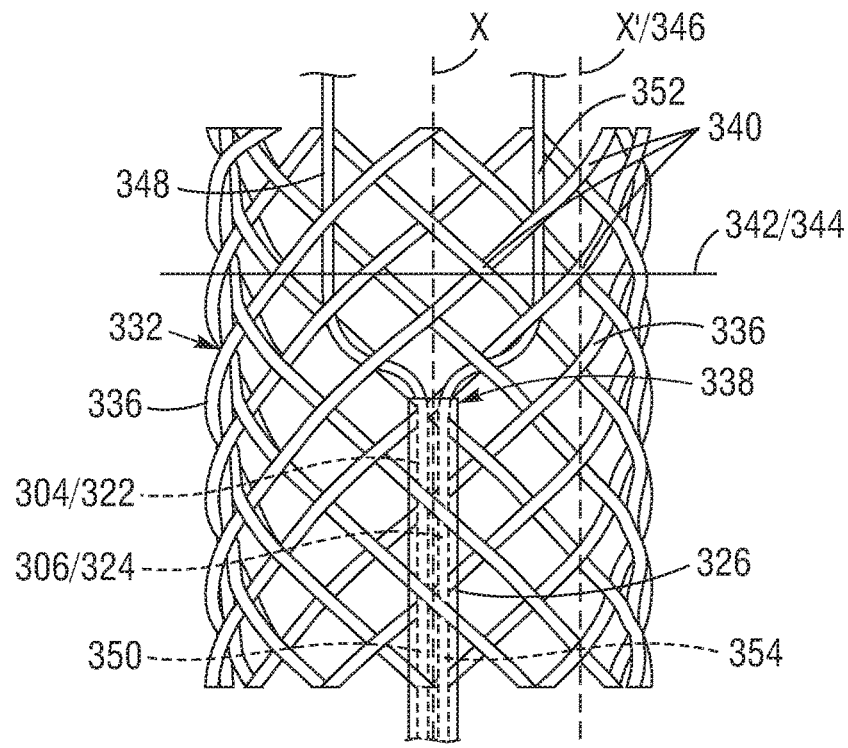
FIG. 18 is a top plan view of a portion of a braided layer of the catheter device of FIG. 17.
Figure 19:
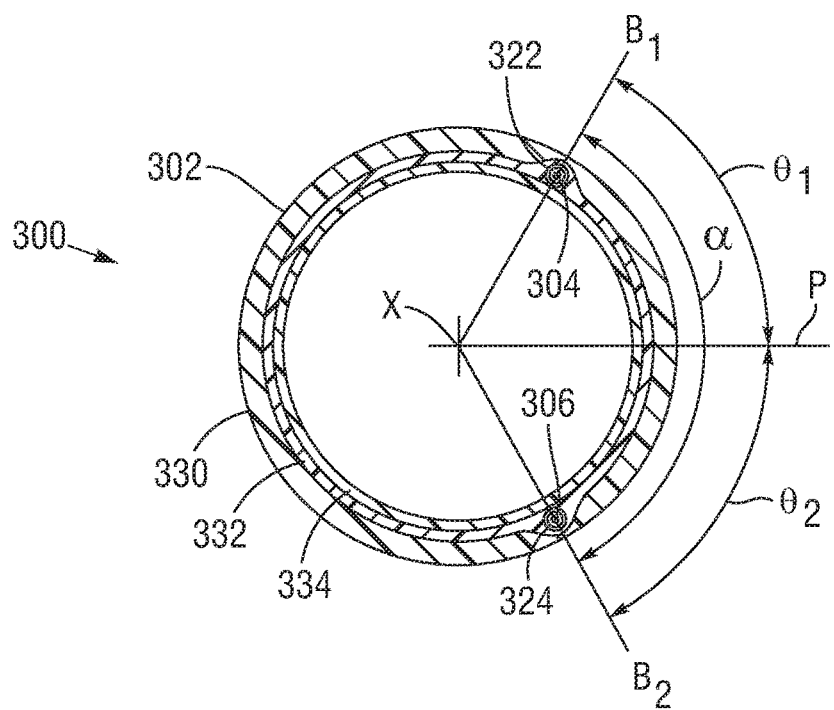
FIG. 19 is a cross-sectional view of the catheter device of FIG. 17, taken along line 19-19 of FIG. 17.
Figure 26:
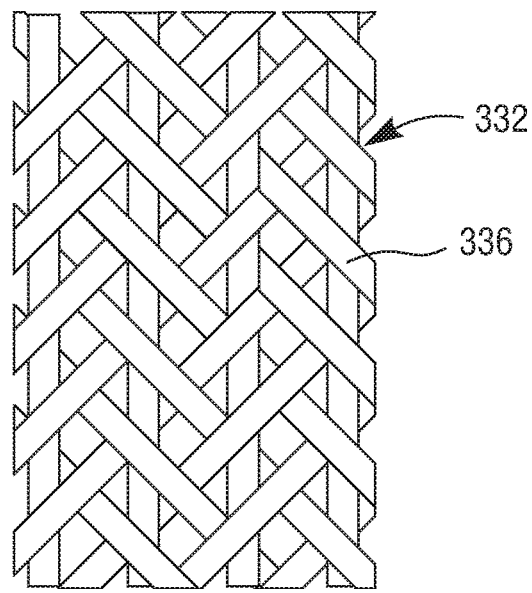
FIG. 26 illustrates another embodiment of the braided layer of the catheter device of FIG. 17 in which the braid members are braided in a triaxial braid.

In certain embodiments, the second layer 332 can be a braided layer, as best shown in FIG. 18. The braided layer 332 can comprise a plurality of braid members 336 (e.g., metallic, natural, or synthetic wires, fibers, filaments, yarns, threads, etc.). The braided layer 332 can have any desired number of braid members 336, which can be oriented along any suitable number of carrier axes and braided together. For example, the braid members 336 can be braided together in a biaxial braid, as shown in FIG. 18, braided in a triaxial braid, as shown in FIG. 26, or in any other braid pattern. The following discussion proceeds with reference to the biaxial braid illustrated in FIG. 18 for ease of illustration, but the configurations described herein can be applicable to a braid having any suitable braid pattern.

Figure 21:
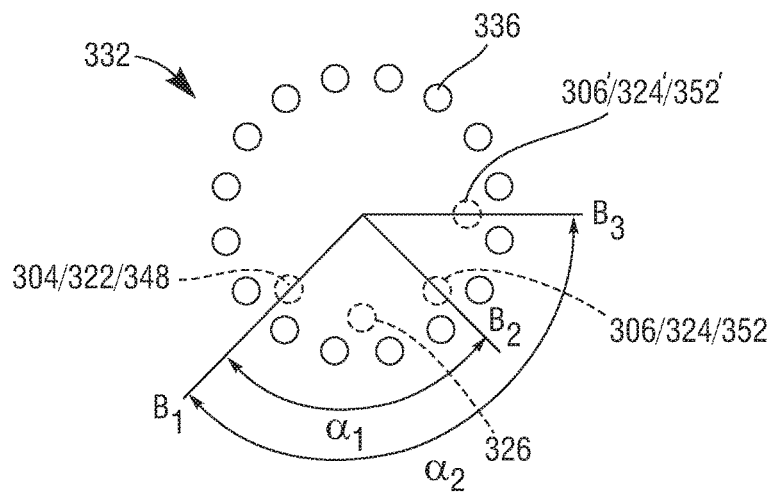
FIG. 21 is a schematic cross-sectional view of the braided layer of the catheter device of FIG. 17 illustrating representative positions of the pull wires in the distal portion of the catheter device.

The braid members 336 of the braided layer 332 can cross over or under one another at points of intersection, referred to herein as "picks" 340. The picks 340 can be angularly spaced from each other about the circumference of the braided layer 332, with the angular separation corresponding to, for example, the number of braid members 336 and the number of axes in which the braid members are arranged. For example, a braided layer including 16 braid members 336 braided in a triaxial braid can have eight picks spaced 45° apart about the circumference of the braided layer, as best shown in FIG. 21.

Returning to FIG. 18, for purposes of this application, a "row" of picks refers to picks 340 that are located at the same longitudinal distance along the axis X of the shaft 302. Thus, for example, the picks 340 located along a plane 342 perpendicular to the axis X define a row 344 of picks. For purposes of this application, picks 340 aligned with one another along an axis parallel to the axis X of the shaft 302 are referred to as a "column" of picks. Thus, the picks 340 located along the axis X' define a column 346 of picks.

Still referring to FIG. 18, the pull-wire conduit 326 can be incorporated into the braided layer 332. For example, in some embodiments, braid members 336 oriented in one or more directions can pass over the pull-wire conduit 326, while braid members 336 oriented in one or more other directions can pass underneath the pull-wire conduit, as illustrated in FIG. 18. In other embodiments, the pull-wire conduit 326 can be located beneath the braided layer 332 such that all of the braid members 336 in the braid pass over the pull-wire conduit.

The pull-wire conduit 326 can be incorporated into the braided layer such that the pull-wire conduit extends along a selected column of picks 340. Upon exiting the pull-wire conduit 326, the lumens 322, 324 and, thus, the pull wires 304, 306, can diverge away from each other while remaining incorporated into the braided layer 332. Alternatively, the lumens 322, 324 can be removed from the braid and reintroduced into the braid distally of the pull-wire conduit 326, as described in greater detail with respect to the embodiment of FIGS. 22-25. In certain configurations, the pull-wire lumens 322, 324 can diverge from one another in increments related to the spacing of the picks 340. For example, in FIG. 18, the lumen 322 can diverge from the pull-wire conduit 326 such that a distal portion 348 of the lumen 322 (and, thus, of the pull wire 304) is angularly offset from a proximal portion 350 of the lumen 322 by two columns 346 of picks 340. In the illustrated embodiment, the angular divergence occurs over the space of two rows 344 of picks 340, although the transition may occur over any suitable number of rows, as desired. The second pull wire 306 and lumen 324 can diverge from the pull-wire lumen 326 by the same number of rows 344 and columns 346 of picks 340, but in the opposite direction from the first pull-wire lumen 322, such that a distal portion 352 of the lumen 324 is angularly offset from a proximal portion 354 of the lumen by two columns 344 of picks 340. In this manner, the distal portions 348, 352 of the lumens 322, 324 can be spaced apart from each other symmetrically about the pull-wire conduit 326.

FIGS. 19 and 21 show the angular positioning of the distal portions 348, 352 of the two pull-wire lumens 322, 324 (and, thus, the pull wires 304, 306) along an arc defined by the side wall of the shaft 302. Referring to FIG. 19, the first pull-wire lumen 322 can be positioned along a first axis $B_1$ extending radially from the central axis X of the shaft 302 to the first lumen 322. The second pull wire lumen 324 can be positioned along a second axis $B_2$ extending radially from the central axis X of the shaft 302 to the second lumen 322. As shown, the distal portions 348, 352 of the lumens 322, 324 are spaced angularly apart from one another by angle α between axes $B_1$ and $B_2$ along an arc defined by the side wall of the shaft. The angle α can be any angle greater than zero degrees and up to 360 degrees. In the embodiment shown, the angle α is about 120°.

In embodiments where the pull-wire lumens 322, 324 are aligned along columns 346 of picks 340 of the braided layer 332, the axes $B_1$ and $B_2$ can intersect the columns 346 of picks such that the angle α depends on the angular spacing between the columns of picks. For example, with reference to FIG. 21, a tubular braided layer 332 including 16 braid members 336 braided in a triaxial pattern can include eight picks 340 spaced along its circumference. In this configuration, each pick 340 is separated from the neighboring picks by about 45°. FIG. 21 schematically illustrates one configuration in which the first pull-wire lumen 322 is offset from the pull-wire conduit 326 by one column of picks (e.g., located between respective braid members 336 in FIG. 21), and is intersected by axis $B_1$. The second pull-wire lumen 324 also diverges from the pull-wire conduit 326 by one column of picks, and is intersected by the axis $B_2$. This results in an angular separation $α_1$ of 90° between the respective distal portions 348, 352 of the lumens 322, 324.

By offsetting the distal portions 348, 352 of the lumens 322, 324 from the conduit 326 by an equal number of columns 346 of picks 340, angular spacing of 90° (one column each), 180° (two columns each), 270° (three columns each), and 360° (four columns each) can be achieved. The distal portions 348, 352 of the lumens 322, 324 can also be offset from one another by different numbers of columns 346. For example, if one lumen (e.g., lumen 322) is offset by n columns 346, the other lumen (e.g., lumen 324) can be offset by n+1 columns. One representative example of this configuration is also illustrated in FIG. 21, in which the lumen 322 is offset from the conduit 326 by one column and intersected by axis $B_1$, and the second lumen (indicated by 324') is offset from the conduit by two columns in the opposite direction and intersected by axis $B_3$. In a triaxial braid with 16 braid members 336, this results in an angular spacing $α_2$ of 135° between the respective distal portions 348, 352'. Following the formula where one lumen is offset by n columns 346, and the other lumen is offset by n+1 columns, angular spacings of 135°, 225°, and 315° can be achieved.

Figure 20:
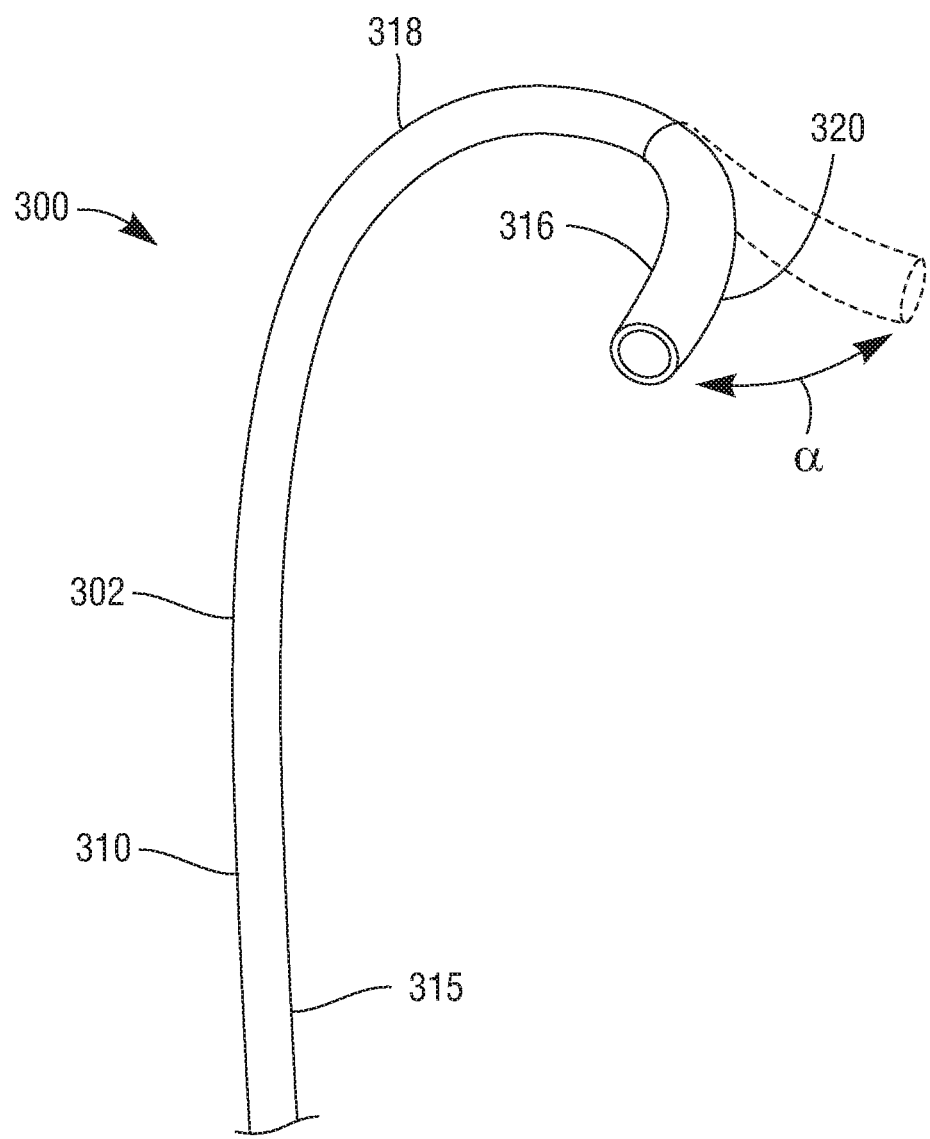
FIG. 20 is a perspective view of the catheter device of FIG. 17, showing the ability of the distal tip portion to flex at various angles within a range of flexion (a) of the distal top portion.

With reference to FIG. 20, this dual wire configuration allows the shaft 302 to have a primary flexing section (corresponding to the proximal section 318 of the steerable distal portion 316) and secondary flexing section (corresponding to the distal section 320 of the steerable distal portion 316). In some embodiments, a durometer of the primary flexing section 318 is about the same as, higher than, or lower than a durometer of the secondary flexing section 320 depending on a desired relative flexibility between the two sections. The primary flexing section has a lower durometer than the main shaft, which is the portion of the shaft 302 proximal of the primary flexing section in the illustrated embodiment that is substantially not steerable. In some embodiments, the main shaft has a higher durometer than the secondary flexing section which, in turn, has a higher durometer than the primary flexing section.

When one or both pull wires 304, 306 are under tension, the primary flexing section 318 flexes or curves in a respective flexing plane P (FIG. 19). By virtue of the pull wires 304, 306 extending through the lumens 322, 324 in close proximity to each other proximally of the steerable distal portion 316, tensioning either one or both pull wires is effective to adjust the curvature of the primary flexing section 318 in its respective flexing plane P. By applying differential tension to the pull wires, the secondary flexing section 320 can be caused to flex in various different directions relative to the primary flexing section 318. For example, applying the same amount of tension to each pull wire 304, 306 causes the secondary flexing section 320 to curve in the same plane P as the primary flexing section. Increasing tension in the first pull wire 304 relative to the second pull wire 306 causes the secondary flexing section 320 to curve or bend in a first direction away from the plane P of the primary flexing section 318 (shown in solid lines in FIG. 20). Likewise, increased tension in the second pull wire 306 relative to the first pull wire 304 causes the secondary flexing section 320 to curve or bend in a second direction, opposite the first direction, away from the plane P of the primary flexing section 318 (shown in phantom in FIG. 20).

In the illustrated embodiment, the secondary flexing section 320 permits a distal tip of the catheter device 300 to access a locus approximated by a portion of a surface of a sphere defined by a first range of flexion and a second range of flexion, which in some embodiments corresponds to the angular components of a spherical coordinate system. The first range has an angular width or azimuthal width a (see, e.g., FIGS. 19 and 21) (bounded by the radial axes $B_1$ and $B_2$). The second range has polar angle with a minimum at or near the X axis (about 0°) and a maximum dependent on the durometer and length of the secondary flexing section 320 (maximally flexed state). Accordingly, tensioning pull wire 304, optionally while partially untensioning pull wire 306, flexes the secondary flexing section 320 radially outwards generally along axis $B_1$. Similarly, pull wire 306 is operable to flex the secondary flexing section 302 along axis $B_2$. By adjusting the relative tensions between the pull wires 304, 306, the distal tip of the catheter device 300 can be steered to any intermediate location or point in this space.

The secondary flexing section 320 can thus be made to flex in any radial flexing plane within angle α. The angular positioning of the pull wires 304, 306 thus defines the azimuthal or first range of flexion a for the secondary flexing section 320. In the embodiment shown in FIG. 19, this direction of flexion can be in any plane between about −60° and about +60° relative to the primary flexing plane, wherein the 0° direction is the primary flexing plane P. Accordingly, in this case, the first range of flexion a is about 120°. In embodiments such as FIGS. 19 and 21, where the pull wires 304, 306 are spaced apart in a braided layer according to the columns 346 of picks 340 along which they are aligned, the angle α and the corresponding first range of flexion can be about 90° (e.g., about −45° to about +45°), about 180 degrees (e.g., about −90° to about +90°), etc. In other embodiments, the angle α and the corresponding first range of flexion can vary, such as about 140° (about −70° to about +70°), about 130° (about −65° to about +65°), about 110° (about −55° to about +55°), about 100° (about −50° to about +50°), about 90° (about 45° to about +45°), about 80° (about −40° to about +40°), about 70° (about −35° to about +35°), or about 60° (about −30° to about +30°).

In other embodiments, the first range of flexion of the secondary flexing section 320 need not be symmetrical relative to the primary flexing plane P. For example, the portion of the first pull wire 304 in the distal portion 348 of the first lumen 322 can be angularly spaced from the pull-wire conduit 326 (and the primary flexing plane P) by a first angle $θ_1$, and the portion of the second pull wire 306 in the distal portion 352 of the second lumen 324 can be angularly spaced from the pull-wire conduit 326 (and the primary flexing plane P) by a second angle $θ_2$, wherein $θ_1$ and $θ_2$ are not equal to each other. In this manner, the first range of flexion of the secondary flexing section 320 encompasses the primary flexing plane P but can be adjusted to extend further on one side of the primary flexing plane P than the other.

Incorporating the pull wires into a braided layer can provide significant advantages over known catheter systems. For example, traditional methods of including multiple pull wires angularly spaced from one another about the circumference of a catheter shaft require a groove defined in a mandrel to hold the pull wire (or a spacer mandrel) during manufacture of the catheter. However, if it is desired that the pull wire curve from one angular location to another, locating the pull wire in a correspondingly curved groove in the mandrel would cause the pull wire to lock the catheter to the mandrel, complicating removal of the mandrel from the catheter. Incorporating the pull wires into a braided layer eliminates this problem, and allows the pull wires to change direction multiple times, and at any location.

During fabrication of the catheter device 300, the braid members 336 can be braided such that the pull-wire conduit 326 is incorporated into the braid, as described above. When the braid reaches the distal end of the pull-wire conduit 326 (which can be positioned, for example, at a location where a change in deflection direction is desired), the braiding can be temporarily halted, and the lumens 322, 324 (and, thus the pull wires 302, 304) can be removed from the braid. The lumens 322, 324 can be moved to the desired location (e.g., locations corresponding to specified columns 346 of picks 340), and the braiding process can be resumed. In embodiments where one lumen is offset by n columns 346, and the other lumen is offset by n+1 columns (e.g., to create an angle α of 135°), the catheter body can be rotated in the braiding machine (e.g., while the braid and the pull-wire conduit 326 are held stationary) such that the angles $\theta_1$ and $\theta_2$ are equal (e.g., about 67.5° in the present example).

FIGS. 22-25 illustrate another embodiment of a catheter device 400 comprising a shaft 402 having a proximal portion (not shown) and a steerable distal portion 418, similar to the embodiments of FIGS. 16 and 17 above. The catheter device can include a first pull wire 404, a second pull wire 406, and a third pull wire 408. The shaft can be coupled to a handle including one or more adjustment mechanisms for increasing and decreasing tension in the pull wires 404-408 to flex and unflex the distal portion 418 of the shaft, as described above. The distal portion 418 can have a proximal section 422 (also referred to as a primary flexion section) that is configured to flex in a primary flex direction, and a distal section 424 (also referred to as a secondary flexing section) that is steerable in the manner of section 320 of the shaft 302 of FIG. 20. The durometer and flexibility of the different portions of the shaft 402 can be selected according to the flexion characteristics desired, as described above.

Figure 22:
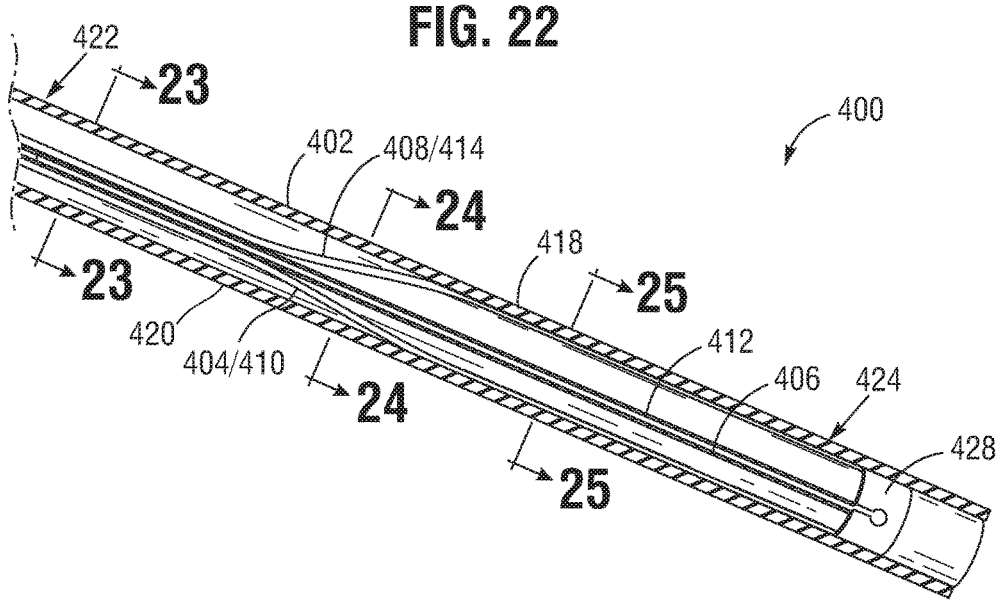
FIG. 22 is a cross-sectional side view of a distal end portion of another embodiment of a catheter device including three pull wires.
Figure 23:
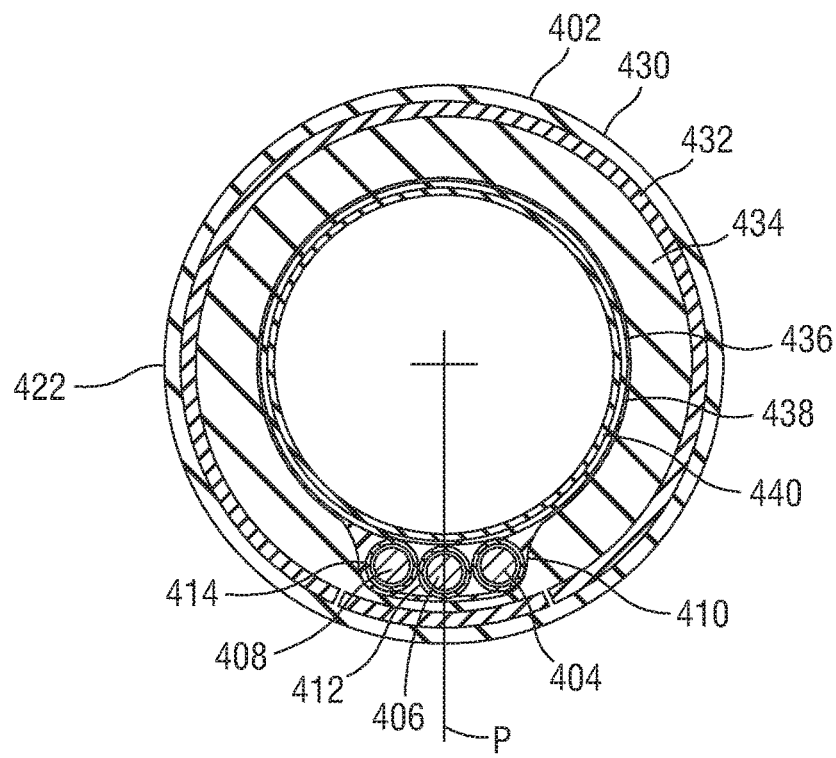
FIG. 23 is a cross-sectional view of the catheter device of FIG. 22 taken along line 23-23 of FIG. 22.

Referring to FIGS. 22 and 23, the pull wires 404, 406, 408 can be disposed in respective pull-wire lumens 410, 412, 414. The pull wires 404-408 and lumens 410-414 can be grouped together, and can extend along a wall of the shaft 402 at least through the proximal portion of the shaft and through the proximal section 422 of the distal portion 418. At a selected location along the shaft 402 (e.g., a divergence location 420 located between the proximal section 422 and the distal section 424 of the distal portion 418 of the shaft), the lumens 410-414 (and, thus, the pull wires 404-408) can angularly diverge from each other about the circumference of the shaft 402. More specifically, the first pull-wire lumen 410 and the third pull-wire lumen 414 can diverge from the second pull-wire lumen 412 in opposite directions. Meanwhile, the second pull-wire lumen 412 can continue to extend longitudinally along the shaft. The pull wires 404-408 can be coupled to a pull ring 428 at or near the distal end of the catheter shaft 402, on which the pull wires can act when tensioned to steer the catheter shaft, as described above. In other embodiments, the pull wires 404-408 and the lumens 410-414 can be disposed in a pull-wire conduit similar to the conduit 326 of FIG. 17.

The shaft 402 can include a first or outer layer 430, a second layer 432, a third layer 434, a fourth layer 436, a fifth layer 438, and a sixth or inner layer 440. The layers 430, 432, 434, 438, and 440 can be made of any of a variety of materials. For example, in some embodiments the second layer 432 can be a laser-cut metal tube, the first and third layers 430, 434 can be polymeric materials such as Pebax®, and the sixth layer 440 can be a liner made from, for example, PTFE. In some embodiments, the first and third layers 430, 434, can be a single layer with the laser-cut metal tube 432 embedded within it. In the illustrated embodiment, the fourth layer 436 can be configured as a braided layer, and the lumens 410-414 (and, thus, the pull wires 404-408) can be incorporated into the braided layer 436 in the manner described above with respect to FIGS. 16-21. In some embodiments, the pull-wire lumens 410-414 can extend along a column of picks of the braided layer 436 until the lumens reach the divergence location 420.

FIG. 23 is a cross-sectional view taken along line 23-23 of FIG. 22, and illustrates the pull wires and lumens incorporated into the braided layer 436. As the pull wires reach the divergence location 420, the first and third pull-wire lumens 410, 414 can leave the braided layer 436 as they angularly diverge from the second pull-wire lumen 412. In other words, the first and third pull-wire lumens 410, 414 can be disposed radially outwardly of the braided layer 436 along the portion of the shaft 402 along which the lumens diverge. The first and third pull-wire lumens 410, 414 can then be reintroduced into the braided layer 436 at, for example, the location along the shaft where the lumens reach a selected angular offset from the second pull-wire lumen 412.

Figure 24:
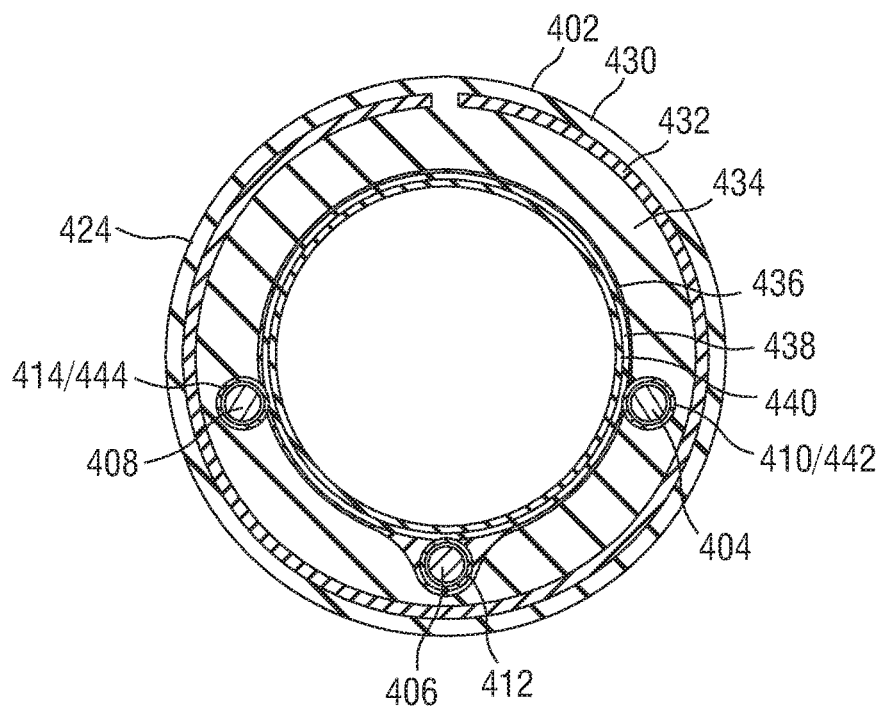
FIG. 24 is a cross-sectional view of the catheter device of FIG. 22 taken along line 24-24 of FIG. 22.

For example, in one embodiment the first and third pull-wire lumens 410, 414 can be removed from the braided layer 436 at or near the divergence location 420. The first pull-wire lumen 410 can then angularly diverge from the second pull-wire lumen 412, and can be disposed radially outwardly of the braided layer 436. Referring to FIG. 24, an intermediate portion 442 of the first pull-wire lumen 410 is disposed radially outwardly of the braided layer 436, and is at least partially incorporated into the third layer 434. Meanwhile, the third pull-wire lumen 414 also diverges from the second pull-wire lumen 412 in the opposite direction from the first pull-wire lumen 410. As shown in FIG. 24, an intermediate portion 444 of the third pull-wire lumen 414 is also disposed radially outwardly of the braided layer 436. At the location shown in FIG. 24, each of the first and third pull-wire lumens 410, 414 has diverged from the second pull-wire lumen 412 by an angle of about 75°. In the illustrated embodiment, the second pull-wire lumen 412 remains incorporated in the braided layer 436 along the portion of the shaft where the first and third pull-wire lumens diverge.

Figure 25:
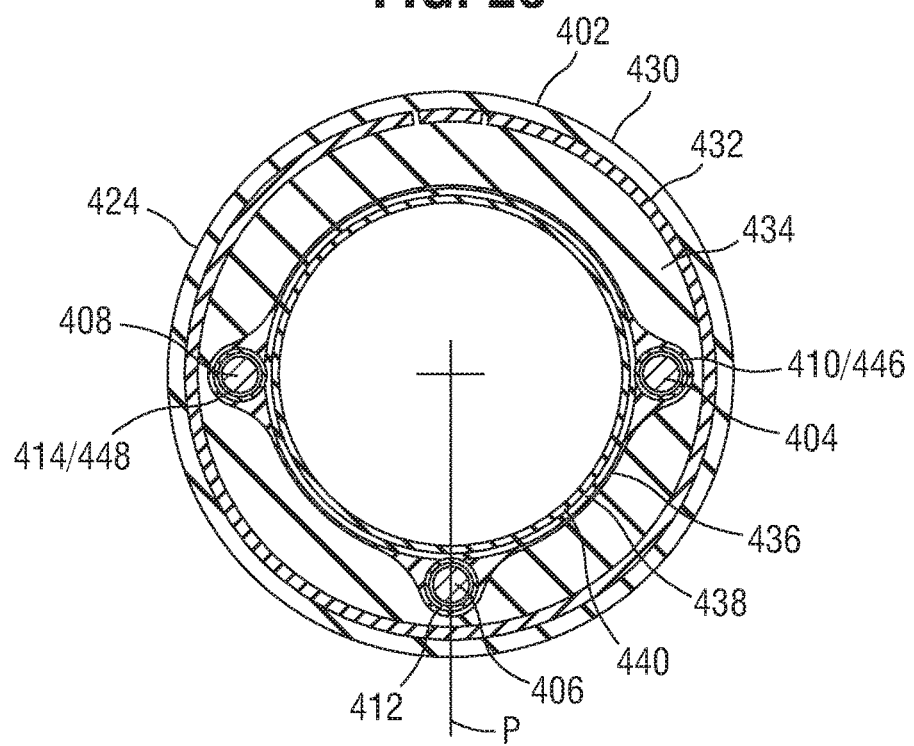
FIG. 25 is a cross-sectional view of the catheter device of FIG. 22 taken along line 25-25 of FIG. 22.

When the first and third pull-wire lumens 410, 414 reach a selected amount of angular separation from the second pull-wire lumen 412 (e.g., corresponding to a selected number of picks of the braided layer 436), the first and third pull-wire lumens can be re-introduced into the braided layer 436. For example, FIG. 25 is a cross-sectional view of the shaft taken along line 25-25 of FIG. 22 illustrating a distal portion 446 of the first pull-wire lumen 410 reincorporated into the braided layer 436. A distal portion 448 of the third pull-wire lumen 414 can also be reincorporated into the braided layer 436.

In the illustrated embodiment, the first pull-wire lumen 410 can be offset from the second pull-wire lumen 412 by about 90°. The third pull-wire lumen 414 can also be offset from the second pull-wire lumen 412 by about 90°, resulting in an angular separation of 180° between the first pull-wire lumen 410 and the third pull-wire lumen 414 in the distal section 424 of the shaft. Thus, in an exemplary embodiment where the braided layer 436 includes 16 braid members braided in a triaxial braid including eight picks, the first pull-wire lumen 410 (and, thus, the first pull wire 404) is offset from the second pull-wire lumen 412 (and, thus, the second pull wire 406) by two columns of picks. The third pull-wire lumen 414 (and, thus, the third pull wire 408) is also offset from the second pull-wire lumen 412 by two columns of picks.

When the pull wires 404-408 are under tension, the primary flexing section 422 flexes or curves in a respective flexing plane P, which can be aligned with (e.g., can intersect) the second pull wire 406, as shown in FIGS. 23 and 25. Tensioning one or all of the pull wires is effective to adjust the curvature of the primary flexing section 422 in its respective flexing plane P, and applying differential tension to the pull wires can cause the secondary flexing section 424 to flex in various different directions relative to the primary flexing section 422, in a manner similar to the embodiment of FIG. 20. In certain configurations, because the second pull wire 406 extends all the way to the pull ring 428 along the primary flexing plane P, the second pull wire 406 can allow the distal portion 418 of the shaft (e.g., the primary flexing section 422 and/or the secondary flexing section 424) to achieve a greater degree of flexion in the direction of the flexing plane P than can be achieved with two pull wire configurations where the pull wires diverge from the flexing plane P.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, the term "coupled" generally means physically coupled or linked and does not exclude the presence of intermediate elements between the coupled items absent specific contrary language.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A delivery apparatus for implanting a prosthetic implant in a native lumen of the body, the apparatus comprising:
   a handle portion;
   a first shaft extending from and movable relative to the handle portion, the first shaft comprising a proximal end portion coupled to the handle portion and a distal end portion;

a second shaft extending from the handle portion and coaxially disposed within the first shaft, the second shaft comprising a proximal end portion coupled to the handle portion and a distal end portion configured to mount a prosthetic implant in a radially compressed state;

the handle portion comprising a steering assembly configured to move the first shaft longitudinally relative to the second shaft while concurrently flexing the second shaft;

wherein the steering assembly further comprises a rotatable member coupled to the proximal end portion of the first shaft such that rotation of the rotatable member causes corresponding proximal and distal motion of the first shaft relative to the second shaft;

wherein the rotatable member is coupled to the distal end portion of the second shaft by a pull wire such that rotation of the rotatable member causes corresponding flexing and unflexing of the distal end portion of the second shaft.

2. The delivery apparatus of claim 1 wherein the rotatable member is coupled to the proximal end portion of the first shaft by a threaded shaft movably coupled to the rotatable member and a coupling member disposed on the threaded shaft and coupled to the first shaft.

3. The delivery apparatus of claim 2, wherein the rotatable member includes a threaded tubular portion configured to receive and engage the threaded shaft such that rotation of the rotatable member causes proximal and distal motion of the threaded shaft relative to the rotatable member.

4. The delivery apparatus of claim 1, wherein the pull wire is coupled to a pull wire coupling member movably disposed on a threaded shaft coupled to the rotatable member such that rotation of the rotatable member causes corresponding longitudinal motion of the pull wire coupling member along the threaded shaft.

5. The delivery apparatus of claim 4, wherein the steering assembly further comprises a pull wire guide member positioned to guide the pull wire radially away from the second shaft to the pull wire coupling member.

6. The delivery apparatus of claim 5, wherein the pull wire extends proximally from the pull wire guide member to the pull wire coupling member, and proximal motion of the pull wire coupling member along the threaded shaft causes flexing of the second shaft.

7. The delivery apparatus of claim 5, wherein the pull wire guide member is coupled to a side portion of the handle portion and extends perpendicular to a longitudinal axis of the handle portion.

8. The delivery apparatus of claim 4, wherein the handle portion further comprises at least one guide member extending parallel to the threaded shaft and operatively connected to the pull wire coupling member to prevent rotation of the pull wire coupling member as it moves along the threaded shaft.

9. The delivery apparatus of claim 1, wherein the first shaft comprises a tubular member defined by a plurality helically wound filaments.

10. The delivery apparatus of claim 9, wherein the tubular member further comprises a retaining portion located proximally of a distal end portion of the tubular member, and the filaments are independently movable relative to one another along at least a portion of the tubular member extending between the retaining portion and the distal end portion.

11. The delivery apparatus of claim 9, wherein the distal end portion of the tubular member is shape-set to have predetermined curvature.

12. The delivery apparatus of claim 1, wherein:
the second shaft comprises a braided layer; and
the pull wires extend at least partially within the braided layer.

* * * * *